(12) United States Patent
Ramael et al.

(10) Patent No.: US 7,510,881 B2
(45) Date of Patent: Mar. 31, 2009

(54) METHOD AND KIT FOR THE QUANTITATIVE AND/OR QUALITATIVE DETECTION OF COMPONENTS IN A SAMPLE

(76) Inventors: Marc Ramael, W. Van Doornyckstraat 28, B-9120 Haasdonk (BE); Jean-Paul Sanders, Nieuwstraat 99, B-2560 Kessel (BE)

( * ) Notice: Subject to any disclaimer, the term of this patent is extended or adjusted under 35 U.S.C. 154(b) by 316 days.

(21) Appl. No.: 10/569,713

(22) PCT Filed: Aug. 25, 2003

(86) PCT No.: PCT/EP03/09393

§ 371 (c)(1),
(2), (4) Date: Feb. 24, 2006

(87) PCT Pub. No.: WO2005/019820

PCT Pub. Date: Mar. 3, 2005

(65) Prior Publication Data

US 2006/0286546 A1 Dec. 21, 2006

(51) Int. Cl.
*G01N 33/543* (2006.01)
(52) U.S. Cl. ........................ 436/518; 435/7.1; 435/7.92; 435/7.94; 435/969; 436/524; 436/525; 436/540
(58) Field of Classification Search ............... 435/6, 435/7.1, 7.5, 7.92–7.95, 969, 973; 436/501, 436/518, 524–527, 540, 164
See application file for complete search history.

(56) References Cited

U.S. PATENT DOCUMENTS

| 4,868,109 | A | * | 9/1989 | Lansdorp | .................... 435/7.1 |
| 5,223,242 | A | | 6/1993 | Khaw et al. | |
| 5,296,347 | A | * | 3/1994 | LaMotte, III | .................... 435/5 |
| 5,583,001 | A | | 12/1996 | Bobrow et al. | |
| 6,110,687 | A | * | 8/2000 | Nilsen | ........................... 435/6 |
| 2002/0031781 | A1 | | 3/2002 | Khaw et al. | |
| 2003/0008410 | A1 | * | 1/2003 | Hechinger | .................. 436/172 |

OTHER PUBLICATIONS

Böcher, et al. "Synthesis of Mono- and Bifunctional Peptide—Dextran Conjugates for the Immobilization of peptide Antigens on ELISA Plates: Properties and Application," *Journal of Immunological Methods*, vol. 208, pp. 191-202, 1997.
Okadome, et al. "Reactivity of a Dual Amplified Chlamydia Immunoassay with Different Serovars of *Chlamydia trachomatis*," *International Journal of STD & AIDS*, vol. 10, pp. 460-463, 1999.
Torchilin, et al. "Antibody-Linked Chelating Polymers for Immunoimaging in vivo," *Journal of Controlled Release*, No. 11, pp. 297-303, 1989.
Werther, et al. "Immunoglobulin and Enzyme-Conjugated Dextran Polymers Enhance u-PAR Staining Intensity of Carcinoma Cells in Peripheral Blood Smears," *The Journal of Histochemistry & Cytochemistry*, vol. 47, No. 7, pp. 959-963, 1999.
International Search Report, dated Dec. 12, 2003.

* cited by examiner

*Primary Examiner*—Gail R Gabel
*Assistant Examiner*—Gary W Counts
(74) *Attorney, Agent, or Firm*—Knobbe, Martens, Olson & Bear, LLP

(57) ABSTRACT

A method and kit for quantitatively and/or qualitatively detecting one or more components in samples, including the use of metal-particle labelled reagents and an antibody conjugate are disclosed. The components are capable of binding to a probe. A kit and method for staining components in cell and tissue sections, based upon the detection method, are also disclosed.

13 Claims, No Drawings under 35 U.S.C.
METHOD AND KIT FOR THE QUANTITATIVE AND/OR QUALITATIVE DETECTION OF COMPONENTS IN A SAMPLE

RELATED APPLICATIONS

This application is the U.S. National Phase under 35 U.S.C. §371 of International Application PCT/EP2003/009393, filed Aug. 25, 2003.

FIELD OF THE INVENTION

The present invention relates to the field of diagnostic assays and kits for the detection of biological molecules.

BACKGROUND TO THE INVENTION

Micro-arrays are tools for DNA and RNA molecular diagnostics. Detection of nucleic acids is possible using parallelisation techniques thereby enabling the investigation of several thousands of sequences in one reaction or experiment. Most applications focus on expression profiling for measuring adequately the expression of several thousands genes of interest. Detection of molecular binding on micro-arrays is visualized by use of special fluorescent dyes such as Cy3 and Cy5. Visualization of the binding is limited by the stability of the fluorescent marker, and in order to evaluate the processed micro-arrays, highly sophisticated and expensive laser scanning devices are required in addition to highly sophisticated software for analysing the data generated by laser scanning devices.

For the last thirty-five years, metal particles including gold and silver have been used as both contrast enhancement agents or light absorption labels in many different types of analytic and/or diagnostic applications. The great majority of these applications fall under the category of cytoimmunochemistry studies which have used gold or silver enhanced gold particles as markers to study structural aspects of cellular, subcellular, or tissue organization. In these studies, metal particles are usually detected and localized by electron microscopy, including scanning, transmission, and BEI (backscattered electron imaging). These methods take advantage of the electron dense nature of metals or the high atomic number of metals to facilitate the detection of the gold particles by virtue of the large numbers of secondary and backscattered electrons generated by the dense metal (see; Hayat, Immunogold-silver staining reference Page 1 and Chapters 1, 6-15; and Hayat, Colloid Gold reference Chapters 1, 5, 7 and others).

A number of patents describe the use of enzymatic methods or gold-based technology on micro-arrays to detect the presence of specific sequences of DNA. PCT patent application number WO 00/72018 (EP 1 179 180) (Advanced Array Technologies) describes the use of biotinylated DNA as probes against DNA samples immobilised on a glass micro-array, using gold (10 nm) labelled streptavidin as a visualisation agent.

US 2001/0010906A1 describes optimisation of capture probes design for sandwich hybridisation on solid carrier.

EP 1 164 201 describes the use of inverted detection for identifying and/or quantifying nucleotide target sequences on biochips using micro-fluidity techniques.

EP 1 096 024 describes a method for detection of homologue sequences after multiplex PCR for detecting *Staphylococcus* microorganisms.

AU8366001, AU7547501, CA2397280, WO0196604, AU736340, U.S. Pat. No. 6,214,560, CN1282378T, EP1023456, EP1021554, AU1294399, WO9920789 disclose a similar technique using gold labelled streptavidin particles of at least 80 nm for visualisation of bound nucleic acids on a glass micro-array using back scattered light.

U.S. Pat. No. 5,583,001, U.S. Pat. No. 196,306 and U.S. Pat. No. 5,731,158 disclose the use of in situ amplification techniques wherein the signal generated by the bound probe is amplified and visualised using enzymatic or gold based techniques. The catalysed amplification reporter deposit (CARD) technique was found to result in a signal amplification ranging from 10 to 100 fold and found to give equal results as the polymer based technique. The principle of CARD is widely used for several applications including electron microscopy, immunohistochemistry, ELISA, and in situ hybridization. The use of gold in a CARD based amplification has been described for the above mentioned techniques but real signal amplification on micro-arrays is not disclosed using gold or an enzymatic based technology.

U.S. Pat. No. 6,451,980 discloses a technique for signal enhancement of bi-specific antibody-polymer probe for use in immunoassay. Therein is described the use of bispecific antibodies where one part of the antibody complex recognises the antigen and the other part binds the polymer probe consisting of a poly-L-lysine backbone coated with "detectable signals".

WO0206511 and AU8292001 (Genisphere) disclose an amplification technique applicable on micro-arrays, consisting of a dendrimer-based approach. Dendrimers are DNA molecules marked with a fluorescent dye. The special feature is that those molecules can form three dimensional structures by a type of hybridisation which results in a supermolecule heavily marked with Cy3 or Cy5 molecules. This leads to an enormous amplification of the signal generated by the bound nucleic acid of interest.

EP 1 230 396 and WO 01/36681 (Digene) disclose a technology detecting DNA/RNA hybrids on micro-arrays using a specific monoclonal antibody directed specifically to RNA/DNA hybrids with visualisation using fluorescent dyes.

WO 96/14314 disclose the use of a specific monoclonal antibody detecting DNA/PNA nucleic acid hybrids in solution and on a solid support.

For the detection of low concentrations of molecule components in the field of diagnostics, the methods of chemiluminescence and electrochemiluminescence are widely used. These methods provides a means to detect low concentrations of components by amplifying the number of luminescent molecules or photon generating events manyfold, the resulting "signal amplification" then allowing for detection of low concentration components. However, the above mentioned methods of signal amplification have associated limitations which makes the detection of components by these methods complicated, not easy to use, time consuming, and costly.

Problems of interference of chemical or enzymatic reactions, contamination, complicated and multi-step procedures, limited adaptability to single step "homogeneous" (non-separation) formats, and the requirement of costly and sophisticated instrumentation are areas that those in the art are constantly trying to improve.

Improvements has so far failed to provide means for the quantative and/or qualitative detection of molecules such as DNA, RNA, proteins, polypeptides without an evaluation step requiring an additional device such as a laser scanner, equipment to measure scattered light and/or specialised software. A low cost means of detection of components in samples is of importance in everyday fields of environmental science, veterinary medicine, pharmaceutical research, food and water quality control and the like. Furthermore a means which is simple to use, obviates the need for specialised training in equipment and/or protocols. Furthermore, the detection of substances at low concentrations (less than about 1 picomole substance/sample volume analyzed) is presently not possible without the use of fluorescent, luminescent, chemiluminescent, or electrochemiluminescent labels and other detection methods, all of which require optical reading devices to evaluate results.

It is a purpose of this invention not only to overcome the present day limitations, for example the disadvantages of light scattering-based diagnostic assays, but to also overcome the limitations and disadvantages of other non-light scattering methods such as signal amplification. This invention as described herein is easier to use, has greater detection sensitivity, and is capable of measuring components in samples across a wider concentration range than was previously possible. The present invention is broadly applicable to most sample types and assay formats as a signal generation and detection system for components.

The present invention provides a signal and detection system for the detection of components where the procedures can be simplified and the amount and types of steps and reagents reduced. The present invention provides for the quantitative and/or qualitative detection of single or multiple components in a sample. The present invention also provides for substantial reductions in the number of different tests and amounts of sample material that are analysed. Such reduction in the number of individual tests leads to reduced cost and waste production, especially medically-related waste that must be disposed of.

SUMMARY OF THE INVENTION

One embodiment of the present invention is a method for quantitatively and/or qualitatively detecting one or more components in one or more samples, said component capable of binding to a probe, comprising the steps in the following order:

a) applying one or more samples onto a solid support, b) optionally storing solid supports of step a) at a temperature between 0 and 10 degrees Celsius, c) incubating solid support of step a) or b) with one or more tagged probes, d) incubating solid support with a monoclonal or polyclonal antibody directed against the tag of step c), said antibody raised in species A and said antibody optionally labelled with metal particle, e) incubating solid support with antibody conjugate, said polymer comprising:
  one or more antibodies, anti-A, directed against immunoglobulins of species A,—one or more antibodies, anti-B, directed against immunoglobulins of species B,
  optionally one or more substances which directly or indirectly cause a quantitative colour change compared with the solid support, f) incubating the solid support with a polypeptide capable recognition by anti-B antibodies, said polypeptide labelled with one or more substances which directly or indirectly cause a quantitative colour change compared with the solid support, and g) optionally incubating the solid support with a metal enhancement reagent and/or a colour change reagent that is a suitable substrate of an enzyme attached to the antibody conjugate, and h) reading the solid support to quantitatively and/or qualitatively detect said components.

Another embodiment of the present invention is a method as described above wherein step a) is
  a) applying one or more probes onto a solid support, and step c) is
  c) incubating solid supports with tag-labelled sample, Another embodiment of the present invention is a method as described above wherein step c) is absent and step d) is
  d) incubating solid supports with metal-particle-labelled anti-component monoclonal or polyclonal antibody, said antibody raised in species A.

Another embodiment of the present invention is a method as described above further comprising the steps, after step f), of:
  f-1) repeating steps e) to f), and
  f-2) optionally repeating step f-1).

Another embodiment of the present invention is a method as described above wherein the solid support is supplied with probe pre-applied, and step a) is not performed by the user.

Another embodiment of the present invention is a method as described above wherein the reading of step h) comprises the use of a colour chart.

Another embodiment of the present invention is a method as described above wherein the reading of step h) comprises the use of a device suitable for detecting changes in conductance and/or current across the solid support at the positions at which said samples are applied.

Another embodiment of the present invention is a kit for quantitatively and/or qualitatively detecting one or more components in one or more samples, said component capable of binding to a probe, comprising:

a) one or more solid supports, b) a container in which a quantity antibody conjugate is present, said conjugate comprising:
  one or more antibodies, anti-A, directed against immunoglobulins of species A,—one or more antibodies, anti-B, directed against immunoglobulins of species B,
  optionally one or more substances which directly or indirectly cause a quantitative colour change compared with the solid support.

Another embodiment of the present invention is a kit as described above further comprising a container in which a quantity of anti-tag polyclonal or monoclonal antibodies is present, said antibodies raised in species A.

Another embodiment of the present invention is a kit as described above wherein the solid support is pre-loaded with probes capable of binding to said components.

Another embodiment of the present invention is a kit as described above for use in a method as described above.

Another embodiment of the present invention is a kit according as described above for use in detecting, diagnosing and/or monitoring the progress of a Human Papillomavirus (HPV) infection and wherein one or more molecular probes is capable of binding to an HPV component.

Another embodiment of the present invention is a kit as described above wherein said component is a coat polypeptide.

Another embodiment of the present invention is a kit as described above wherein said component is a gene selected from the group consisting of HPV 16, HPV18, HPV 31, HPV 33, HPV 35, HPV 52 and HPV 58.

Another embodiment of the present invention is a kit as described above for use in detecting, diagnosing and/or monitoring the progress of one or more of the disease states in humans as listed in Table 1, by detecting a polypeptide and/or nucleic acid corresponding to the listed component.

Another embodiment of the present invention is a kit as described above for use in detecting, diagnosing and/or monitoring the progress infections caused by one or more of one or more of HCV, HIV, HBV, HTLV, mycobacteria, *Staphylococcus aureus*.

Another embodiment of the present invention is a kit as described above for use in detecting, diagnosing and/or monitoring the progress neurodegenerative diseases by detecting one or more of beta-amyloids, hTAU, phosphoTAU and APOE.

Another embodiment of the present invention is a kit as described above for use in detecting, diagnosing and/or monitoring the progress of malignant diseases, autoimmunity or allergy related diseases by detecting one or more of ANA, Jo-1, Myeloperoxidase, RNP, Scl-70, Sm, SS-A, IgE, IgG-subclasses and circulating antibodies.

Another embodiment of the present invention is a kit as described above for use in environmental testing of water for bacteria.

Another embodiment of the present invention is a kit as described above for use in environmental testing of food components for genetically modified components, *listeria* and *salmonella*.

Another embodiment of the present invention is a method for staining components in cell and/or tissue sections suitable for visualisation using microscopy comprising the steps of:

j) incubating said section with one or more tagged probes directed against a component, k) incubating said section with metal labelled anti-tag monoclonal or polyclonal antibody, said antibody raised in species A, l) incubating said section with antibody/enzyme polymer, said polymer comprising at least:
  one or more antibodies, anti-A, directed against immunoglobulins of species A,—one or more antibodies, anti-B, directed against immunoglobulins of species B,
  optionally one or more substances which directly or indirectly cause a quantitative colour change, m) incubating the section with a polypeptide capable recognition by anti-B antibodies, said polypeptide labelled with one or more substances which directly or indirectly cause a quantitative colour change, and n) optionally incubating the section with a metal enhancement reagent and/or a colour change reagent that is a suitable substrate of an enzyme attached to the antibody conjugate.

Another embodiment of the present invention is a method as described above wherein step j) is absent and step k) is k) incubating section with metal particle labelled anti-component monoclonal or polyclonal antibody, said antibody raised in species A.

Another embodiment of the present invention is a method as described above further comprising the steps, after step m), of:

m-1) repeating steps l) to m), and m-2) optionally repeating step m-1).

Another embodiment of the present invention is a kit for staining components in cell and/or tissue sections suitable for visualisation using microscopy comprising:

a container in which a quantity of antibody/enzyme polymer antibody, said polymer comprising at least:
  one or more antibodies, anti-A, directed against immunoglobulins of species A,—one or more antibodies, anti-B, directed against immunoglobulins of species B,
  optionally one or more substances which directly or indirectly cause a quantitative colour change.

Another embodiment of the present invention is a kit as described above further comprising a container in which a quantity of anti-tag polyclonal or monoclonal antibodies is present, said antibodies raised in species A.

Another embodiment of the present invention is a kit as described above for use in a method as described above.

Another embodiment of the present invention is a method as described above, and a kit according as described above wherein said metal particle is gold.

Another embodiment of the present invention is a method as described above, and a kit as described above wherein said tag is biotin.

Another embodiment of the present invention is a method as described above, and a kit as described above wherein said polypeptide capable recognition by anti-B antibodies is labelled with gold particles and/or alkaline phosphatase.

DETAILED DESCRIPTION OF THE INVENTION

The present invention is related to a method for the quantitative and/or qualitative detection of components in a sample, using a solid support, an antibody conjugate, a tagged probe directed to said components, and an antibody directed against said tag.

A "sample" as used herein means any sample that contains one or more components to be tested, said components capable of binding to a probe enabling identification of said component. Examples of samples or components include, but are not limited to DNA, cDNA, mRNA, RNA, nucleic acids, proteins, polypeptides, glycoproteins, receptors, ligands, metabolites, toxins etc. Other examples of samples include, but are not limited to blood, blood components, other bodily fluids, tissues, drinking water, soil, domestic waste, industrial waste, any food stuff—liquid or solid, crops.

A "probe" as used herein means any compound capable of specific binding to a component. For example, a nucleic acid oligomer binding to a gene, a ligand binding to a receptor are examples of probe/component interactions according to the invention. According to the present invention, the affinity of binding between a probe and a component is better than 10 uM, 5 uM, 2 uM, 1 uM, 0.1 uM, 0.01 uM or 1 nM. Examples of probes include but are not limited to nucleic acids, PNAs, proteins, peptides, antibodies, ligands, receptors etc.

A "tag" as used here means any type of substance which is capable of being recognised by an antibody. Examples of such tags include, but are not limited to polypeptides, proteins, polysaccharides, amino acids, vitamins (such as biotin), natural or synthetic substances, enzymes (such as AP and HRP), dyes (such as FITC and TR), nucleic acids, PNA, DNP, digoxygenin, streptavidin, Psoralen. A "tag" as used here also means a metal, metals or organometallic substances. According to one aspect of the invention, the probe is tagged.

According to another aspect of the invention, the sample is tagged. The process of tagging is known to the skilled artisan and can be performed on proteins, peptides or nucleic acids. For example, nucleic acid may be biotinylated by performing a polymerase chain reaction on the sample using biotinylated primer(s) specific for the gene of interest. Peptides and proteins may be biotinylated using biotinylation reagents which, for example, biotinylate the C-terminus, the N-terminus and/or reactive side chains of the protein or peptide. The present invention includes any method of the art or future methods for the tagging of sample.

By "solid support" herein is meant any solid support which is capable of immobilising components and/or samples. Such solid supports are known in the art and include, but are not limited to, nitrocellulose, glass slides, nylon, silane coated slides, nitrocellulose coated slides, plastics. The solid support preferably comprises nitrocellulose.

Antibodies as used according to the present invention may be whole antibodies or may be part of an antibody, said part comprising at least the complementary determining region and, where necessary, a species-specific region that can be recognised by other antibodies (e.g. a constant region).

An "antibody conjugate" refers to a complex comprising a bridging compound with an antibody directed against antibodies raised in one species (anti-A, e.g. against part of the constant region of mouse antibodies) and/or an antibody directed against antibodies raised in a different species (anti-B, e.g. against part of the constant region of rabbit antibodies). Attachment may be by covalent or non-covalent means. Examples of species against which said attached antibodies may be raised include, but are not limited to rabbit, human, goat, mouse, rat, cow, calf, camel, llama, monkey, donkey, guinea pig, chicken and sheep.

According to an aspect of the invention the bridging compound is a soluble polymeric support such as, for example, dextran, polyethylene glycol, agarose, acrylamide, protein, carbohydrate, any bio-polymer, and synthetic polymer, nucleic acid, PNA, latex or any other known or future polymeric subustance. Optionally also attached to the bridging compound are one or more substances that directly or indirectly cause a quantitative colour change compared with the solid support. Said substances may be coloured, or are capable of inducing colour change. For example, the substance might be a dye, a metal particle, a non-metal particle, or an enzyme that catalyses a colour-change reaction. It is within the scope of the invention that a combination of the aforementioned colour change substances are attached to the bridging compound.

A colour change according to the invention is a change in the colour or intensity of colour of the solid support at the location at which the sample is applied (e.g. from white to black, from white to red, from white to grey, from white to blue, etc.)

The anti-tag antibody as used in the present invention can be any antibody or part thereof containing a complementary-determining-region that is capable of binding to the tag. The anti-tag antibody may optionally be labelled with one or more substances that are coloured (e.g. a dye, a metal particle), or are capable of inducing colour change (e.g. an enzyme that catalyses a colour-change reaction.)

Examples of suitable dyes according to the invention, include but are not limited to FITC, TR, Cy3, Cy5, Rhodamine, RPE, APC, DAPI, RPE-Cy5, PE, Fast Green, Alexins, Tamra, Joe, Rox, 6-FAM, HEX, TET, Dabcyl, TEG.

Examples of suitable metal particles according to the invention, include but are not limited to gold, silver, iron, nickel, gadolinium, lead, uranium, caesium, platinum, rhodium, technetium, tellurium, selenium, silicon (silicium), cupper, tin, rhenium, europium, aluminium, germanium, chromium, cadmium, niobium, titanium, magnesium, manganese, molybdenum, antimony, americium, lithium, wolfram, and all metallic substances conducting or semi-conducting.

Enzymes that catalyse colour change and that are suitable according to the invention may be any used in a colour change assay such as an ELISA or Western blot, and includes, but is not limited to alkaline phosphatase, horse radish peroxidase beta-galactosidase, luciferase, NADH. Reagents involved in visualising the colour change are known to the skilled addressee and include, but are not limited to DAB, TMB, ABTS, AEC, OPD, Fast Red, fuchsine, AP-blue, AP-orange, BCIP, NBT, pNPP, BCI-NBT, CSPD, CDP-STAR, INT-BCIP.

The present invention is also related to the finding that the use of metal particle-labeled strepavidin or antibodies in a method of the invention, said metal particle having a diameter 0.6 to 40 nm together with metal enhancement, surprisingly leads to an improvement in quantitative and/or qualitative colour change, or conductance change.

The present invention is related to the finding that the use of metal-particle-labeled probes, said metal particle having a diameter 0.6 to 40 nm and metal enhancement, in combination with the aforementioned conjugate for staining tissues and cells surprisingly leads to enhanced quantitative and/or qualitative colour change, or conductance change.

By metal enhancement is known to the skilled artisan in the field, and refers to an enhancement of signal by means of metal precipitation due to reduction. Means to enhance the signal include the use of metals such as silver and nickel as secondary reagents. One embodiment of the present invention is a method for quantitatively and/or qualitatively detecting one or more components in one or more samples, said component capable of binding to a probe, comprising the steps in the order of:

a) Applying one or more samples onto a solid support, b) Optionally storing solid support at a temperature between 0 and 10 degrees Celcius, c) Incubating solid support with one or more tagged probes, d) incubating solid support with a monoclonal or polyclonal antibody directed against the tag of step c), said antibody raised in species A, and said antibody optionally labelled with metal particle, e) Incubating spotted solid support with antibody conjugate, said conjugate comprising:
   one or more antibodies, anti-A, directed against immunoglobulins of species A,
   one or more antibodies, anti-B, directed against immunoglobulins of species B,
   optionally one or more substances which directly or indirectly cause a quantitative and/or qualitative colour change compared with the solid support, f) incubating the solid support of step e) with a polypeptide capable of recognition by anti-B antibodies, said polypeptide labeled with one or more substances which directly or indirectly cause a quantitative colour change, g) optionally incubating the solid support with a metal enhancement reagent and/or a colour change reagent that is a suitable substrate of an enzyme attached to the antibody conjugate, and h) reading the solid support to quantitatively and/or qualitatively detect said components.

By "applying" as used herein in reference to applying one or more samples or probes to a solid support, is meant deposition of one or more synthetic or biological substances on a solid support. The deposition may be by a manual method or by using a device, resulting in an action including, but not limited to spotting, pipetting, printing, jet printing, dropping etc.

By "reading" as used herein means determining from the change in the properties of the solid support at the position where the sample or probe is applied, the concentration of the components. According to the invention a change in the property of the solid support may be a colour change and/or a change in electrical conductivity or electrical current at the position where the sample or probe is applied.

Reading may mean using normal vision to ascertain a colour change (e.g. from white to red, from white to black, from white to grey) on the matrix to determine the presence or absence of a component i.e. a qualitative reading. Reading may also mean using normal vision to ascertain a colour change to determine the concentration of a component i.e. a qualitative reading. It is within the scope of the invention that the reading may be taken using a colour chart that allows a comparison of the colour of the sample with that of known concentrations of probe or component. It is within the scope of the invention that a colour change disclosed herein may be read with or without the aid of electronic and optical measuring equipment. For example, a colour change of the solid support may be read by means of a reflectance reader as discussed below.

Using a reflectance reader to measure a colour change leads to accurate measurements and allows the determination of the concentration of the probe or component. The concentration of an unknown component can be calculated by interpolation on a standard curve obtained with several concentrations of probe or component.

Reading may also mean using a device to measure a change of electrical conductivity or electrical current at the position on the solid support where the sample or probe is applied, to determine the concentration of the components. The inventors have found that the use of metal-labelled reagents according to the invention (e.g. metal-labeled antibody conjugate, metal-labelled polypeptide capable of recognition by anti-B antibodies) can result in a change of electrical conductivity or electrical current of the solid support. The change can be conveniently and accurately read using a device capable of detecting a change in conductivity and/or current across a solid support. Said device may comprise one or more of the following features: one or more electrical contact probes, circuitry to measure conductivity and/or current, an analogue to digital converter. According to one example, one probe of the device contacts an upper surface of the solid support at the position where the sample or probe is applied, and a second probe contacts the same position on the lower surface; the conductivity and/or current across said probes is measured by the device. According to another example, one probe of the device contacts an upper surface of the solid support at the position where the sample or probe is applied, and the whole of the lower surface of the solid support contacts a conducting plate; the conductivity and/or current across said probe and plate is measured by the device. The latter example has the convenience that the measurement of more than one sample requires movement of only the probe contacting the upper surface.

In one aspect of the invention, the samples are applied to the solid support without the addition of any extra reagents to the sample prior to the application of sample. In another aspect of the invention, the samples are applied to the solid support after a preconditioning procedure which increases the concentration of salt in said samples. The salt may be any dissociating salt in the art, including, but not limited to sodium chloride, potassium chloride. The preconditioning may comprise the addition of a volume of salt solution of a known concentration to a volume of sample. The preconditioning step may comprise the addition of a volume of salt solution of a known concentration to an unknown volume of sample. The concentration of salt in the sample may be adjusted to lie in the range of 100 mM to 500 mM, 500 mM to 1 M, 1 M to 1.5M, 1.5M to 2M, 2M to 2.5M, 2.5M to 3M, 3M to 3.5M, 3.5M to 4 M, 3.5 M to 5 M, 0.5 M to 2.5 M, 0.5 M to 3 M, 0.5 M to 4 M.

In another aspect of the invention, the sample is applied to the solid support at one or more positions with the same sample at the same relative concentration. In another aspect of the invention, the sample is applied to the solid support at one or more positions at the different relative concentrations. In another aspect of the invention, the sample is applied to the solid support at one or more positions at the same and/or different relative concentrations.

In another aspect of the invention, the temperature at which the solid support on which sample has been applied is optionally stored in step b) is between 0 and 10 degrees Celsius, 2 and 10 degrees, 3 and 10 degrees Celsius, 4 and 10 degrees Celsius, 5 and 10 degrees Celsius, 6 and 10 degrees Celsius, 7 and 10 degrees Celsius, 0 and 5 degrees Celsius, 1 and 5 degrees Celsius, 2 and 5 degrees Celsius, 3 and 5 degrees Celsius, 1 degree Celsius, 2 degrees Celsius, 3 degrees Celsius, 4 degrees Celsius, 5 degrees Celsius, 6 degrees Celsius, 7 degrees Celsius, 8 degrees Celsius, 9 degrees Celsius, 10 degrees Celsius.

In another aspect of the invention, when the metal particle is gold, the gold may be of any diameter. In another aspect, the gold may have an average diameter of 0.6, 0.8 nm, 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm and 0.6 to 1.0 nm, 1.0 to 5.0 nm, 5.0 to 10 nm, 10 to 15 nm, 15 to 20 nm, 20 to 25 nm, 25 to 30 nm, 30 to 35 nm, 35 to 40 nm.

In another aspect of the invention, after applying the sample in step a), step b) is performed without drying or baking the samples. In another aspect of the invention, the samples applied to the solid support in step a) are allowed to dry. Methods of drying samples are known in the art and can include, but are not limited to, drying in the air, drying in a incubator, drying in an chamber under low pressure optionally heated. According to another aspect of the invention, the samples applied to the solid support are baked by exposed to a temperature of between 60 to 70 degrees Celsius, 65 to 75 degrees Celsius, 70 to 80 degrees Celsius, 75 to 85 degrees Celsius, 80 to 90 degrees Celsius, 65 degrees Celsius, 70 degrees Celsius, 75 degrees Celsius, 80 degrees Celsius, 85 degrees Celsius or 90 degrees Celsius. The exposure time may be for no more than 10 minutes, 15 minutes, 20 minutes, 25 minutes, 30 minutes, 35 minutes, 40 minutes, 45 minutes, 50 minutes, 55 minutes or 60 minutes. The samples may be dried and then baked, only dried, only baked.

The introduction of wash steps in the method above, may be determined by the skilled artisan in accordance with commonly understood protocols in immunoassays such as ELISA and Western blots. For example, one or more wash steps may be introduced after one or more incubation step, using with a washing reagent such as a buffer. Examples of wash steps are provided in the Examples section.

The use of an antibody conjugate as described herein leads to a surprising signal enhancement accompanied by an insignificant or absent increase of background signal which could not have been anticipated by the skilled artisan. Indeed, the inventors have tested other sandwich type assays which do not use the antibody conjugate, and found an accompanying increase in background signal and the introduction of artefacts. The use of the antibody conjugate as disclosed herein, as found by the inventors, provides signal amplification without a concomitant increase in background signal.

The "metal enhancement reagent" of step g) is any metal-containing reagent wherein the metal precipitates due to reduction. Examples include but are not limited to a silver enhancement reagent by Aurion (the Netherlands), BBI (UK), Sigma-Aldrich (USA), or Amersham (UK).

The "polypeptide capable of recognition by anti-B antibodies" in step f) can be any polypeptide or substance which is recognised by the anti-B antibody attached to the antibody conjugate of step e). If it is a polypeptide, it might be an antibody raised in species B, or an antigenic part thereof. If it is another substance, it might be polysaccharides, amino acid, natural or synthetic substances, nucleic acids, PNA, which is capable of binding to the complimentary determining region of the anti-B antibody of step e).

The components in the samples may be measured qualitatively or quantitatively determined by reading the solid support by measuring a change in property of the solid support at the position where the sample was applied (e.g. measuring a colour change and/or a change in electrical conductivity/current). The change in property may be caused by the dye, the metal, the metal after metal enhancement and/or the colour produced after the enzyme catalyses a colour change reagent. It is an aspect of the invention that the change in property is caused by the metal without metal enhancement. It is an aspect of the invention that the change in property is caused by the dye alone. It is an aspect of the invention that the change in property is caused by metal using metal enhancement. It is an aspect of the invention that the change in property is caused by an enzyme-linked colour change. It is an aspect of the invention that the change in property is caused by one or more of the aforementioned aspects.

In another aspect of the invention, the use of tagged-probe as described in a method above is circumvented by using an antibody raised in species A directly against a component in the sample. Thus, in this embodiment of the invention, step c) as described above is absent, and step d) reads:

d) incubating solid supports with metal-particle labelled anti-component monoclonal or polyclonal antibody, said antibody raised in species A.

The use of an antibody directed against a component in a sample obviates the need for an additional step in which a tagged probe is added, and for an additional assay reagent, the introduction of which can lead to handling error.

In another aspect of the invention, one or more probes are immobilized onto the solid support and one or more samples applied thereto. Thus, the method is performed as described above including the variations disclosed, with steps substituted or performed identically, as indicated in the method comprising the steps in the following order:

a) Applying one or more probes onto a solid support, b) Optionally storing solid supports of step a) at 0 to 10 degrees Celsius, c) Incubating solid support with tagged-sample, d) Incubating solid support with metal-particle-labeled anti-tag monoclonal or polyclonal antibody, said antibody raised in species A, e) Incubating solid support with antibody conjugate, said conjugate comprising:

one or more antibodies, anti-A, directed against immunoglobulins of species A,—one or more antibodies, anti-B, directed against immunoglobulins of species B, optionally one or more substances which directly or indirectly cause a quantitative and/or qualitative colour change compared with the solid support, f) Incubating the solid support with a polypeptide capable recognition by anti-B antibodies, said polypeptide labelled with one or more substances which directly or indirectly cause a quantitative colour change compared with the solid support, and g) optionally incubating the solid support with a metal enhancement reagent and/or a colour change reagent that is a suitable substrate of an enzyme attached to the antibody conjugate, and h) reading the solid support to quantitatively and/or qualitatively detect said components.

According to the above embodiment, the sample is tagged. The process of tagging is known to the skilled artisan and can be performed on proteins, peptides or nucleic acids as discussed above.

In another embodiment, the sample is not tagged, and the component bound to the probe is directly detected using a metal-labelled antibody directed to said component. Thus, the need to tag sample is obviated. In one embodiment of the invention, step c) as described above is absent, and step d) reads:

d) incubating solid supports with metal labelled anti-component monoclonal or polyclonal antibody, said antibody raised in species A.

In another embodiment of the present invention, the solid supports are provided with the probe pre-applied. In one aspect of the invention, the solid support is provided with probe located one or more positions, said probe recognising the same component. In one aspect of the invention, the solid support is provided with probe located one or more positions, said probe recognising different components. Thus, the method of the invention wherein the probe is immobilised onto the solid support is performed from step c). A method in which the solid support is provided with probe pre-applied enables a sample to be assayed for components without the necessity for performing probe application steps. Furthermore, a method using a solid support provided with probe pre-applied, and probe recognising more than one component, enables single samples to be analysed for several components with a single incubation. For example, a single solid support may be used to detect for several cancerous or pre-cancerous conditions as described below by screening a single sample.

It is one advantage of the invention that it does not necessarily require an optical reading device such as a laser scanner or back-scatter measuring equipment, and hence is convenient for use in environments away from laboratory conditions. The invention allows quantitative and/or qualitative results to be obtained at the location at which the sample was taken, for example, in a general practitioner's surgery, in an individual's home, in hospitals, generally 'in the field' without any specialist analytical instruments. Furthermore, the invention provides an assay that is as sensitive as, or more sensitive than assays which use fluorescence. Furthermore, since specialised measuring equipment is not necessarily required, the assay could be performed by a non-specialist.

Another embodiment of the present invention is a method for detecting a component in one or more samples, said method as describe above, further comprising, after step f) the steps of:

f-1) repeating steps e) to f), and f-2) optionally repeating step f-1).

The steps described in the embodiment above are an amplification, which further 30 enhances the sensitivity of the above method, while minimizing the increase in background signal.

Another aspect of the present invention is a kit for the quantitative and/or qualitative detection of components in a sample comprising the following components:

k) one or more solid supports, and l) a container in which a quantity of antibody conjugate as described above is present.

A container may be any sealed or resealable vessel suitable for carrying a quantity of antibody conjugate. Examples include, but are not limited to screw cap vials, push cap vials, break-seal-to-open vials, syringes.

A kit according to the present invention allows a skilled artisan to perform one or more steps of the method disclosed herein, in a convenient manner. The kit may allow a method of the present invention to be performed without the need to measure or determine the concentrations of reagents, so enabling a fast and reproducible assaying of one or more samples.

Another aspect of the present invention is a kit as described above, comprising a solid support according to item k), wherein said support is pre-spotted with one or more molecular probes. In one aspect of the invention, the solid support is provided with probe located one or more positions, said probe recognising the same component. In one aspect of the invention, the solid support is provided with probe located one or more positions, said probe recognising different components. Thus, a kit supplied with solid support in which the molecular probe is pre-applied enables a sample to be assayed for components without the necessity for performing application steps. Furthermore, a kit supplied with solid support pre-spotted with more than one molecule probe, each capable of recognising a different component enables a single sample to be analysed for several components with a single incubation. For example, a single solid support may be used to detect for several pre-cancerous or cancerous conditions as described below by screening a single sample.

Another aspect of the present invention is a kit as disclosed herein, further comprising one or more metal-labelled probes. Each probe may be specific for a component in a sample to be detected.

Another aspect of the present invention is a kit as disclosed herein, comprising antibody conjugate.

Another aspect of the present invention is a kit as disclosed herein, anti-tag antibody raised in species A, said antibody optionally labelled with metal particle.

Another aspect of the present invention is a kit as disclosed herein, a polypeptide capable recognition by anti-B antibodies, said polypeptide labelled with one or more substances which directly or indirectly cause a quantitative colour change compared with the solid support.

Another aspect of the present invention is a kit as disclosed herein comprising one or more additional containers in which reagent necessary for visualisation using the colour change enzyme linked to the antibody conjugate are present.

Another aspect of the present invention is a kit as disclosed herein comprising one or more additional containers in which reagent necessary for the tagging of sample to be tested are present. As already mentioned above, method and reagent for tagging of protein and nucleic acids are known in the art.

Another aspect of the invention is a kit as disclosed herein comprising one or more additional containers in which metal-particle-labelled anti-component antibodies are present.

Another aspect of the invention is a kit as disclosed herein comprising one or more additional containers in which a tagged probe(s) capable of binding to a component(s) is present.

Another aspect of the invention is a kit as disclosed herein comprising one or more additional containers in which a polypeptide capable recognition by anti-B antibodies, said polypeptide labelled with one or more substances which directly or indirectly cause a quantitative colour change compared with the solid support is present.

In another aspect of the invention, the kit enables the skilled person to perform one or more of the method disclosed herein. The kit may comprise one or more additional containers in which reagents are present enabling the skilled person to perform the complete method.

Alternatively, the kit may comprise a minimum number of containers, such as only item 1), for example, that enables a skilled person to perform the method disclosed herein.

In another aspect of the invention, the kit contains instructions for use. In another aspect of the invention the instructions describing a method of the invention as disclosed herein.

In another aspect of the invention, the kit may be used for the diagnosis of disease, susceptibility of disease, monitoring the progress of disease, monitoring the progress of disease during treatment, testing of food, water, soil, testing for contamination, testing for the presence of genetically modified (GM) food components and/or organisms.

Another aspect of the present invention is a method and/or kit as disclosed herein for detecting the presence of a component in a sample by visualisation, wherein the sample to be tested comprises a component related to a disease, and the probe is an antibody directed against the DNA, mRNA, cDNA or polypeptide representing said component or part thereof in the diseased individual. Alternatively, the molecular probe is a nucleic acid (DNA, PNA) oligomer which is capable of hybridizing to the DNA, mRNA, cDNA representing said component or part thereof in the diseased individual. A method and/or kit of the invention uses one or more of the embodiments disclosed herein. Examples of components which are associated with diseases and which are detectable using the method and/or kit of the invention are provided in Table 1.

A method and/or kit according to the present invention may be used for the diagnosis and detection of cancer in individuals, for example, for the diagnosis of a type of cancer, for the early detection of cancer, to monitor the progress of cancer in individuals already diagnosed with the disease, to detect a relapse of cancer. Cancer is still a major disease and to prolong life expectancy, it would be advantageous to detect the disease in a pre-clinical stage. A diagnostic assay as disclosed herein makes this possible. Non-limiting examples of components to which cancer or several hereditary conditions associated with are provided in Table 1 and, one or more of which are detectable using the method and/or kit of the invention. A diagnosis may require detection of one of more of the listed molecules.

TABLE 1

List of components which are disease-related and are detectable using the kit and/or method of the present invention.

| Number | Component | Comments |
|---|---|---|
| 1. | BRCA1 | breast cancer 1, early onset |
| 2. | TP53 | tumor protein p53 (Li-Fraumeni syndrome) |
| 3. | CFTR | cystic fibrosis transmembrane conductance regulator, ATP-binding cassette (sub-family C, member 7) |
| 4. | APP | amyloid beta (A4) precursor protein (protease nexin-II, Alzheimer disease) |
| 5. | APOE | apolipoprotein E |
| 6. | BRCA2 | breast cancer 2, early onset |
| 7. | HBB | hemoglobin, beta |
| 8. | APC | adenomatosis polyposis coli |
| 9. | MYC | v-myc myelocytomatosis viral oncogene homolog (avian) |
| 10. | HD | huntington (Huntington disease) |
| 11. | BCL2 | B-cell CLL/lymphoma 2 |
| 12. | ABL1 | v-abl Abelson murine leukemia viral oncogene homolog 1 |
| 13. | BAX | BCL2-associated X protein |
| 14. | DMD | dystrophin (muscular dystrophy, Duchenne and Becker types), includes DXS142, DXS164, DXS206, DXS230, DXS239, DXS268, DXS269, DXS270, DXS272 |
| 15. | CDKN2A | cyclin-dependent kinase inhibitor 2A (melanoma, p16, inhibits CDK4) |
| 16. | ATM | ataxia telangiectasia mutated (includes complementation groups A, C and D) |
| 17. | TNF | tumor necrosis factor (TNF superfamily, member 2) |
| 18. | RB1 | retinoblastoma 1 (including osteosarcoma) |
| 19. | VEGF | vascular endothelial growth factor |
| 20. | ERBB2 | v-erb-b2 erythroblastic leukemia viral oncogene homolog 2, neuro/glioblastoma derived oncogene homolog (avian) |
| 21. | FGG | fibrinogen, gamma polypeptide |
| 22. | HPRT1 | hypoxanthine phosphoribosyltransferase 1 (Lesch-Nyhan syndrome) |
| 23. | MAPT | microtubule-associated protein tau |
| 24. | MDM2 | Mdm2, transformed 3T3 cell double minute 2, p53 binding protein (mouse) |
| 25. | RUNX1 | runt-related transcription factor 1 (acute myeloid leukemia 1; aml1 oncogene) |
| 26. | SOD1 | superoxide dismutase 1, soluble (amyotrophic lateral sclerosis 1 (adult)) |
| 27. | CDKN1A | cyclin-dependent kinase inhibitor 1A (p21, Cip1) |
| 28. | PAX6 | paired box gene 6 (aniridia, keratitis) |
| 29. | NF1 | neurofibromin 1 (neurofibromatosis, von Recklinghausen disease, Watson disease) |
| 30. | FN1 | fibronectin 1 |
| 31. | CASP3 | caspase 3, apoptosis-related cysteine protease |
| 32. | PAH | phenylalanine hydroxylase |
| 33. | GAPD | glyceraldehyde-3-phosphate dehydrogenase |
| 34. | PTEN | phosphatase and tensin homolog (mutated in multiple advanced cancers 1) |
| 35. | HFE | hemochromatosis |
| 36. | FGFR3 | fibroblast growth factor receptor 3 (achondroplasia, thanatophoric dwarfism) |
| 37. | EGFR | epidermal growth factor receptor (erythroblastic leukemia viral (v-erb-b) oncogene homolog, avian) |
| 38. | DSCR1 | Down syndrome critical region gene 1 |
| 39. | MLH1 | mutL homolog 1, colon cancer, nonpolyposis type 2 (*E. coli*) |
| 40. | PABPC1 | poly(A) binding protein, cytoplasmic 1 |
| 41. | CYP3A5 | cytochrome P450, subfamily IIIA (niphedipine oxidase), polypeptide 5 |
| 42. | PSEN1 | presenilin 1 (Alzheimer disease 3) |
| 43. | FBN1 | fibrillin 1 (Marfan syndrome) |
| 44. | MSH2 | mutS homolog 2, colon cancer, nonpolyposis type 1 (*E. coli*) |
| 45. | AKT1 | v-akt murine thymoma viral oncogene homolog 1 |
| 46. | CCND1 | cyclin D1 (PRAD1: parathyroid adenomatosis 1) |
| 47. | MTHFR | 5,10-methylenetetrahydrofolate reductase (NADPH) |
| 48. | AR | androgen receptor (dihydrotestosterone receptor; testicular feminization; spinal and bulbar muscular atrophy; Kennedy disease) |
| 49. | TGFB1 | transforming growth factor, beta 1 (Camurati-Engelmann disease) |
| 50. | IL6 | interleukin 6 (interferon, beta 2) |
| 51. | KRAS2 | v-Ki-ras2 Kirsten rat sarcoma 2 viral oncogene homolog |
| 52. | HRAS | v-Ha-ras Harvey rat sarcoma viral oncogene homolog |
| 53. | RET | ret proto-oncogene (multiple endocrine neoplasia and medullary thyroid carcinoma 1, Hirschsprung disease) |
| 54. | PPARG | peroxisome proliferative activated receptor, gamma |

TABLE 1-continued

List of components which are disease-related and are detectable using the kit and/or method of the present invention.

| Number | Component | Comments |
|---|---|---|
| 55. | ACTB | actin, beta |
| 56. | CDH1 | cadherin 1, type 1, E-cadherin (epithelial) |
| 57. | ESR1 | estrogen receptor 1 |
| 58. | IGF1 | insulin-like growth factor 1 (somatomedin C) |
| 59. | GSTP1 | glutathione S-transferase pi |
| 60. | IL8 | interleukin 8 |
| 61. | LPL | lipoprotein lipase |
| 62. | FMR1 | fragile X mental retardation 1 |
| 63. | WT1 | Wilms tumor 1 |
| 64. | IL1B | interleukin 1, beta |
| 65. | CYP1A1 | cytochrome P450, subfamily I (aromatic compound-inducible), polypeptide 1 |
| 66. | CTNNB1 | catenin (cadherin-associated protein), beta 1 (88 kD) |
| 67. | ITGA5 | integrin, alpha 5 (fibronectin receptor, alpha polypeptide) |
| 68. | FOS | v-fos FBJ murine osteosarcoma viral oncogene homolog |
| 69. | KIT | v-kit Hardy-Zuckerman 4 feline sarcoma viral oncogene homolog |
| 70. | ATP7B | ATPase, Cu++ transporting, beta polypeptide (Wilson disease) |
| 71. | IGF2 | insulin-like growth factor 2 (somatomedin A) |
| 72. | JUN | v-jun sarcoma virus 17 oncogene homolog (avain) |
| 73. | CYP2C19 | cytochrome P450, subfamily IIC (mephenytoin 4-hydroxylase), polypeptide 19 |
| 74. | BCR | breakpoint cluster region |
| 75. | FGFR2 | fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) |
| 76. | CASP8 | caspase 8, apoptosis-related cysteine protease |
| 77. | INSR | insulin receptor |
| 78. | G6PD | glucose-6-phosphate dehydrogenase |
| 79. | IL4 | interleukin 4 |
| 80. | DRD2 | dopamine receptor D2 |
| 81. | FGFR1 | fibroblast growth factor receptor 1 (fms-related tyrosine kinase 2, Pfeiffer syndrome) |
| 82. | COL1A1 | collagen, type I, alpha 1 |
| 83. | BLM | Bloom syndrome |
| 84. | NF2 | neurofibromin 2 (bilateral acoustic neuroma) |
| 85. | MMP1 | matrix metalloproteinase 1 (interstitial collagenase) |
| 86. | IL2 | interleukin 2 |
| 87. | GRB2 | growth factor receptor-bound protein 2 |
| 88. | BCL2L1 | BCL2-like 1 |
| 89. | PSEN2 | presenilin 2 (Alzheimer disease 4) |
| 90. | TNFRSF6 | tumor necrosis factor receptor superfamily, member 6 |
| 91. | CD44 | CD44 antigen (homing function and Indian blood group system) |
| 92. | MMP9 | matrix metalloproteinase 9 (gelatinase B, 92 kD gelatinase, 92 kD type IV collagenase) |
| 93. | ABCB1 | ATP-binding cassette, sub-family B (MDR/TAP), member 1 |
| 94. | GSTM1 | glutathione S-transferase M1 |
| 95. | IL1A | interleukin 1, alpha |
| 96. | MET | met proto-oncogene (hepatocyte growth factor receptor) |
| 97. | ABO | ABO blood group (transferase A, alpha 1-3-N-acetylgalactosaminyltransferase; transferase B, alpha 1-3-galactosyltransferase) |
| 98. | NRAS | neuroblastoma RAS viral (v-ras) oncogene homolog |
| 99. | NAT2 | N-acetyltransferase 2 (arylamine N-acetyltransferase) |
| 100. | EGR1 | early growth response 1 |
| 101. | TTR | transthyretin (prealbumin, amyloidosis type I) |
| 102. | SOD2 | superoxide dismutase 2, mitochondrial |
| 103. | SCYA2 | small inducible cytokine A2 (monocyte chemotactic protein 1) |
| 104. | NOS3 | nitric oxide synthase 3 (endothelial cell) |
| 105. | CDC2 | cell division cycle 2, G1 to S and G2 to M |
| 106. | STAT1 | signal transducer and activator of transcription 1, 91 kD |
| 107. | SNCA | synuclein, alpha (non A4 component of amyloid precursor) |
| 108. | CLU | clusterin (complement lysis inhibitor, SP-40, 40, sulfated glycoprotein 2, testosterone-repressed prostate message 2, apolipoprotein J) |
| 109. | CDKN1B | cyclin-dependent kinase inhibitor 1B (p27, Kip1) |
| 110. | TYR | tyrosinase (oculocutaneous albinism IA) |
| 111. | MADH4 | MAD, mothers against decapentaplegic homolog 4 (*Drosophila*) |
| 112. | CDK2 | cyclin-dependent kinase 2 |

TABLE 1-continued

List of components which are disease-related and are detectable using the kit and/or method of the present invention.

| Number | Component | Comments |
|---|---|---|
| 113. | MMP3 | matrix metalloproteinase 3 (stromelysin 1, progelatinase) |
| 114. | YWHAZ | tyrosine 3-monooxygenase/tryptophan 5-monooxygenase activation protein, zeta polypeptide |
| 115. | CASP1 | caspase 1, apoptosis-related cysteine protease (interleukin 1, beta, convertase) |
| 116. | PCNA | proliferating cell nuclear antigen |
| 117. | HLA-A, -B, -C | major histocompatibility complex, class I, A, B, C |
| 118. | APOB | apolipoprotein B (including Ag(x) antigen) |
| 119. | CASP9 | caspase 9, apoptosis-related cysteine protease |
| 120. | NOS2A | nitric oxide synthase 2A (inducible, hepatocytes) |
| 121. | IFNG | interferon, gamma |
| 122. | APOA1 | apolipoprotein A–I |
| 123. | AGT | angiotensinogen (serine (or cysteine) proteinase inhibitor, clade A (alpha-1 antiproteinase, antitrypsin), member 8) |
| 124. | ADA | adenosine deaminase |
| 125. | ICAM1 | intercellular adhesion molecule 1 (CD54), human rhinovirus receptor |
| 126. | CYP19 | cytochrome P450, subfamily XIX (aromatization of androgens) |
| 127. | SLC6A4 | solute carrier family 6 (neurotransmitter transporter, serotonin), member 4 |
| 128. | TNFRSF1A | tumor necrosis factor receptor superfamily, member 1A |
| 129. | CD4 | CD4 antigen (p55) |
| 130. | VWF | von Willebrand factor |
| 131. | ACTA1 | actin, alpha 1, skeletal muscle |
| 132. | MECP2 | methyl CpG binding protein 2 (Rett syndrome) |
| 133. | COMT | catechol-O-methyltransferase |
| 134. | TERT | telomerase reverse transcriptase |
| 135. | PKD | polycystic kidney disease 1 (autosomal dominant) |
| 136. | F7 | coagulation factor VII (serum prothrombin conversion accelerator) |
| 137. | PMP22 | peripheral myelin protein 22 |
| 138. | F5 | coagulation factor V (proaccelerin, labile factor) |
| 139. | PPARA | peroxisome proliferative activated receptor, alpha |
| 140. | GCK | glucokinase (hexokinase 4, maturity onset diabetes of the young 2) |
| 141. | MUC1 | mucin 1, transmembrane |
| 142. | SPP1 | secreted phosphoprotein 1 (osteopontin, bone sialoprotein I, early T-lymphocyte activation 1) |
| 143. | RAF1 | v-raf-1 murine leukemia viral oncogene homolog 1 |
| 144. | IGF1R | insulin-like growth factor 1 receptor |
| 145. | IL4R | interleukin 4 receptor |
| 146. | DCC | deleted in colorectal carcinoma |
| 147. | PML | promyelocytic leukemia |
| 148. | PDGFRB | platelet-derived growth factor receptor, beta polypeptide |
| 149. | AGTR1 | angiotensin receptor 1 |
| 150. | UBE3A | ubiquitin protein ligase E3A (human papilloma virus E6-associated protein, Angelman syndrome) |
| 151. | CREBBP | CREB binding protein (Rubinstein-Taybi syndrome) |
| 152. | CYP1B1 | cytochrome P450, subfamily I (dioxin-inducible), polypeptide 1 (glaucoma 3, primary infantile) |
| 153. | AKT2 | v-akt murine thymoma viral oncogene homolog 2 |
| 154. | PLAT | plasminogen activator, tissue |
| 155. | CHRNA7 | cholinergic receptor, nicotinic, alpha polypeptide 7 |
| 156. | TIMP1 | tissue inhibitor of metalloproteinase 1 (erythroid potentiating activity, collagenase inhibitor) |
| 157. | NFKB1 | nuclear factor of kappa light polypeptide gene enhancer in B-cells 1 (p105) |
| 158. | STAT3 | signal transducer and activator of transcription 3 (acute-phase response factor) |
| 159. | CDC42 | cell division cycle 42 (GTP binding protein, 25 kD) |
| 160. | VDR | vitamin D (1,25-dihydroxyvitamin D3) receptor |
| 161. | NTRK1 | neurotrophic tyrosine kinase, receptor, type 1 |
| 162. | VIM | vimentin |
| 163. | TGFBR2 | transforming growth factor, beta receptar II (70–80 kD) |
| 164. | DHFR | dihydrofolate reductase |
| 165. | PTCH | patched homolog (*Drosophila*) |
| 166. | CYP2A6 | cytochnome P450, subfamily IIA (phenobarbital-inducible), polypeptide 6 |
| 167. | HSPCA | heat shock 90 kD protein 1, alpha |
| 168. | E2F1 | E2F transcription factor 1 |
| 169. | CACNA1A | calcium channel, voltage-dependent, P/Q type, alpha 1A subunit |
| 170. | LCK | lymphocyte-specific protein tyrosine kinase |

TABLE 1-continued

List of components which are disease-related and are detectable using the kit and/or method of the present invention.

| Number | Component | Comments |
|---|---|---|
| 171. | LGALS3 | lectin, galactoside-binding, soluble, 3 (galectin 3) |
| 172. | RARA | retinoic acid receptor, alpha |
| 173. | PDZK1 | PDZ domain containing 1 |
| 174. | ALDH2 | aldehyde dehydrogenase 2 family (mitochondrial) |
| 175. | PAX3 | paired box gene 3 (Waardenburg syndrome 1) |
| 176. | FGF2 | fibroblast growth factor 2 (basic) |
| 177. | GJB1 | gap junction protein, beta 1, 32 kD (connexin 32, Charcot-Marie-Tooth neuropathy, X-linked) |
| 178. | LMNA | lamin A/C |
| 179. | CAPN3 | calpain 3, (p94) |
| 180. | ADPRT | ADP-ribosyltransferase (NAD+; poly (ADP-ribose) polymerase) |
| 181. | TUBB | tubulin, beta polypeptide |
| 182. | ABCA1 | ATP-binding cassette, sub-family A (ABC1), member 1 |
| 183. | IL1RN | interleukin 1 receptor antagonist |
| 184. | CTGF | connective tissue growth factor |
| 185. | GSTT1 | glutathione S-transferase theta 1 |
| 186. | DRD4 | dopamine receptor D4 |
| 187. | HTR2A | 5-hydroxytryptamine (serotonin) receptor 2A |
| 188. | FHIT | fragile histidine triad gene |
| 189. | ETV6 | ets variant gene 6 (TEL oncogene) |
| 190. | PDGFB | platelet-derived growth factor beta polypeptide (simian sarcoma viral (v-sis) oncogene homolog) |
| 191. | PPP3R1 | protein phosphatase 3 (formerly 2B), regulatory subunit B (19 kD), alpha isoform (calcineurin B, type I) |
| 192. | TIMP3 | tissue inhibitor of metalloproteinase 3 (Sorsby fundus dystrophy, pseudoinflammatory) |
| 193. | COL1A2 | collagen, type I, alpha 2 |
| 194. | ITGB3 | integrin, beta 3 (platelet glycoprotein IIIa, antigen CD61) |
| 195. | COL3A1 | collagen, type III, alpha 1 (Ehlers-Danlos syndrome type IV, autosomal dominant) |
| 196. | ESR2 | estrogen receptor 2 (ER beta) |
| 197. | B2M | beta-2-microglobulin |
| 198. | SDF1 | stromal cell-derived factor 1 |
| 199. | F9 | coagulation factor IX (plasma thromboplastic component, Christmas disease, hemophilia B) |
| 200. | MAPK14 | mitogen-activated protein kinase 14 |
| 201. | BAK1 | BCL2-antagonist/killer 1 |
| 202. | ITGB1 | integrin, beta 1 (fibronectin receptor, beta polypeptide, antigen CD29 includes MDF2, MSK12) |
| 203. | ACTG1 | actin, gamma 1 |
| 204. | KDR | kinase insert domain receptor (a type III receptor tyrosine kinase) |
| 205. | SCTR | secretin receptor |
| 206. | LEPR | leptin receptor |
| 207. | SP1 | Sp1 transcription factor |
| 208. | CDKN1C | cyclin-dependent kinase inhibitor 1C (p57, Kip2) |
| 209. | MYCN | v-myc myelocytomatosis viral related oncogene, neuroblastoma derived (avian) |
| 210. | IiIL12B | interleukin 12B (natural killer cell stimulatory factor 2, cytotoxic lymphocyte maturation factor 2, p40) |
| 211. | IGF2R | insulin-like growth factor 2 receptor |
| 212. | FLT1 | fms-related tyrosine kinase 1 (vascular endothelial growth factor/vascular permeability factor receptor) |
| 213. | CD36 | CD36 antigen (collagen type I receptor, thrombospondin receptor) |
| 214. | FRD | Friedreich ataxia |
| 215. | COL2A1 | collagen, type II, alpha 1 (primary osteoarthritis, spondyloepiphyseal dysplasia, congenital) |
| 216. | GSN | gelsolin (amyloidosis, Finnish type) |
| 217. | CYP2E | cytochrome P450, subfamily IIE (ethanol-inducible) |
| 218. | APAF1 | apoptotic protease activating factor |
| 219. | ANK1 | ankyrin 1, erythrocytic |
| 220. | SLC6A3 | solute carrier family 6 (neurotransmitter transporter, dopamine), member 3 |
| 221. | CASP7 | caspase 7, apoptosis-related cysteine protease |
| 222. | MYH7 | myosin, heavy polypeptide 7, cardiac muscle, beta |
| 223. | JUNB | jun B proto-oncogene |
| 224. | GHR | growth hormone receptor |
| 225. | IRS1 | insulin receptor substrate 1 |
| 226. | CASP10 | caspase 10, apoptosis-related cysteine protease |
| 227. | BDNF | brain-derived neurotrophic factor |
| 228. | ATP7A | ATPase, Cu++ transporting, alpha polypeptide (Menkes syndrome) |

TABLE 1-continued

List of components which are disease-related and are detectable using the kit and/or method of the present invention.

| Number | Component | Comments |
| --- | --- | --- |
| 229. | TCF1 | transcription factor 1, hepatic; LF-B1, hepatic nuclear factor (HNF1), albumin proximal factor |
| 230. | HGF | hepatocyte growth factor (hepapoietin A; scatter factor) |
| 231. | CYP17 | cytochrome P450, subfamily XVII (steroid 17-alpha-hydroxylase), adrenal hyperplasia |
| 232. | PTPN1 | protein tyrosine phosphatase, non-receptor type 1 |
| 233. | ADRB3 | adrenergic, beta-3-, receptor |
| 234. | TNFSF6 | tumor necrosis factor (ligand) superfamily, member 6 |
| 235. | ERCC5 | excision repair cross-complementing rodent repair deficiency, complementation group 5 (xeroderma pigmentosum, complementation group G (Cockayne syndrome)) |
| 236. | VCAM1 | vascular cell adhesion molecule 1 |
| 237. | TF | transferrin |
| 238. | ACE | angiotensin I converting enzyme (peptidyl-dipeptidase A) 1 |
| 239. | LRP1 | low density lipoprotein-related protein 1 (alpha-2-macroglobulin receptor) |
| 240. | CDK5 | cyclin-dependent kinase 5 |
| 241. | ACACA | acetyl-Coenzyme A carboxylase alpha |
| 242. | TNFRSF1B | tumor necrosis factor receptor superfamily, member 1B |
| 243. | NOTCH3 | Notch homolog 3 (*Drosophila*) |
| 244. | ERBB3 | v-erb-b2 erythroblastic leukemia viral oncogene homolog 3 (avian) |
| 245. | CSK | c-src tyrosine kinase |
| 246. | SCN5A | sodium channel, voltage-gated, type V, alpha polypeptide (long (electrocardiographic) QT syndrome 3) |
| 247. | BCL6 | B-cell CLL/lymphoma 6 (zinc finger protein 51) |
| 248. | FYN | FYN oncogene related to SRC, FGR, YES |
| 249. | CTSK | cathepsin K (pycnodysostosis) |
| 250. | SPARC | secreted protein, acidic, cysteine-rich (osteonectin) |
| 251. | NFKB2 | nuclear factor of kappa light polypeptide gene enhancer in B-cells 2 (p49/p100) |
| 252. | SCYA5 | small inducible cytokine A5 (RANTES) |
| 253. | BMP4 | bone morphogenetic protein 4 |
| 254. | ATP2A2 | ATPase, Ca++ transporting, cardiac muscle, slow twitch 2 |
| 255. | NR3C1 | nuclear receptor subfamily 3, group C, member 1 |
| 256. | THBS1 | thrombospondin 1 |
| 257. | CETP | cholesteryl ester transfer protein, plasma |
| 258. | PTPRC | protein tyrosine phosphatase, receptor type, C |
| 259. | NME1 | non-metastatic cells 1, protein (NM23A) expressed in |
| 260. | TGFBI | transforming growth factor, beta-induced, 68 kD |
| 261. | SREBF1 | sterol regulatory element binding transcription factor 1 |
| 262. | MMP14 | matrix metalloproteinase 14 (membrane-inserted) |
| 263. | KCNQ1 | potassium voltage-gated channel, KQT-like subfamily, member 1 |
| 264. | TUBA1 | tubulin, alpha 1 (testis specific) |
| 265. | SELE | selectin E (endothelial adhesion molecule 1) |
| 266. | ATRX | alpha thalassemia/mental retardation syndrome X-linked (RAD54 homolog, *S. cerevisiae*) |
| 267. | IL2RG | interleukin 2 receptor, gamma (severe combined immunodeficiency) |
| 268. | IGFBP3 | insulin-like growth factor binding protein 3 |
| 269. | JAK3 | Janus kinase 3 (a protein tyrosine kinase, leukocyte) |
| 270. | CSF1R | colony stimulating factor 1 receptor, formerly McDonough feline sarcoma viral (v-fms) oncogene homolog |
| 271. | SHC1 | SHC (Src homology 2 domain containing) transforming protein 1 |
| 272. | CASP4 | caspase 4, apoptosis-related cysteine protease |
| 273. | PLA2G2A | phospholipase A2, group IIA (platelets, synovial fluid) |
| 274. | CXCR4 | chemokine (C—X—C motif), receptor 4 (fusin) |
| 275. | CDKN2B | cyclin-dependent kinase inhibitor 2B (p15, inhibits CDK4) |
| 276. | ARHA | ras homolog gene family, member A |
| 277. | SHH | sonic hedgehog homolog (*Drosophila*) |
| 278. | RARB | retinoic acid receptor, beta |
| 279. | MME | membrane metallo-endopeptidase (neutral endopeptidase, enkephalinase, CALLA, CD10) |
| 280. | CA2 | carbonic anhydrase II |
| 281. | PRKDC | protein kinase, DNA-activated, catalytic polypeptide |
| 282. | HIF1A | hypoxia-inducible factor 1, alpha subunit (basic helix-loop-helix transcription factor) |
| 283. | PRKCA | protein kinase C, alpha |
| 284. | CASP2 | caspase 2, apoptosis-related cysteine protease (neural precursor cell expressed, developmentally down-regulated 2) |

TABLE 1-continued

List of components which are disease-related and are detectable using the kit and/or method of the present invention.

| Number | Component | Comments |
|---|---|---|
| 285. | DMBT1 | deleted in malignant brain tumors 1 |
| 286. | TGFB2 | transforming growth factor, beta 2 |
| 287. | TSC2 | tuberous sclerosis 2 |
| 288. | PSAP | prosaposin (variant Gaucher disease and variant metachromatic leukodystrophy) |
| 289. | XPC | xeroderma pigmentosum, complementation group C |
| 290. | THRA | thyroid hormone receptor, alpha (erythroblastic leukemia viral (v-erb-a) oncogene homolog, avian) |
| 291. | ERCC2 | excision repair cross-complementing rodent repair deficiency, complementation group 2 (xeroderma pigmentosum D) |
| 292. | MAPK1 | mitogen-activated protein kinase 1 |
| 293. | ATP6B1 | ATPase, H+ transporting, lysosomal (vacuolar proton pump), beta polypeptide, 56/58 kD, isoform 1 (Renal tubular acidosis with deafness) |
| 294. | BAG1 | BCL2-associated athanogene |
| 295. | ACHE | acetylcholinesterase (YT blood group) |
| 296. | EGF | epidermal growth factor (beta-urogastrone) |
| 297. | DUSP1 | dual specificity phosphatase 1 |
| 298. | CASP6 | caspase 6, apoptosis-related cysteine protease |
| 299. | THRB | thyroid hormone receptor, beta (erythroblastic leukemia viral (v-erb-a) oncogene homolog 2, avian) |
| 300. | BAD | BCL2-antagonist of cell death |
| 301. | STAT6 | signal transducer and activator of transcription 6, interleukin-4 induced |
| 302. | ELN | elastin (supravalvular aortic stenosis, Williams-Beuren syndrome) |
| 303. | MAOA | monoamine oxidase A |
| 304. | F8 | coagulation factor VIII, procoagulant component (hemophilia A) |
| 305. | ENG | endoglin (Osler-Rendu-Weber syndrome 1) |
| 306. | HSPB1 | heat shock 27 kD protein 1 |
| 307. | HMGCR | 3-hydroxy-3-methylglutaryl-Coenzyme A reductase |
| 308. | PIM1 | pim-1 oncogene |
| 309. | PON1 | paraoxonase 1 |
| 310. | AHR | aryl hydrocarbon receptor |
| 311. | ITGB2 | integrin, beta 2 (antigen CD18 (p95), lymphocyte function-associated antigen 1; macrophage antigen 1 (mac-1) beta subunit) |
| 312. | PTGS1 | prostaglandin-endoperoxide synthase 1 (prostaglandin G/H synthase and cyclooxygenase) |
| 313. | PLCG1 | phospholipase C, gamma 1 (formerly subtype 148) |
| 314. | APOC3 | apolipoprotein C-III |
| 315. | NRG1 | neuregulin 1 |
| 316. | CD14 | CD14 antigen |
| 317. | IRF1 | interferon regulatory factor 1 |
| 318. | ALPL | alkaline phosphatase, liver/bone/kidney |
| 319. | ALDOA | aldolase A, fructose-bisphosphate |
| 320. | XPA | xeroderma pigmentosum, complementation group A |
| 321. | PDGFRA | platelet-derived growth factor receptor, alpha polypeptide |
| 322. | IL5 | interleukin 5 (colony-stimulating factor, eosinophil) |
| 323. | BMP2 | bone morphogenetic protein 2 |
| 324. | GSK3A | glycogen synthase kinase 3 alpha |
| 325. | STK11 | serine/threonine kinase 11 (Peutz-Jeghers syndrome) |
| 326. | GSK3B | glycogen synthase kinase 3 beta |
| 327. | CRYBB1 | crystallin, beta B1 |
| 328. | STAT5A | signal transducer and activator of transcription 5A |
| 329. | SCA1 | spinocerebellar ataxia 1 (olivopontocerebellar ataxia 1, autosomal dominant, ataxin 1) |
| 330. | RXRA | retinoid X receptor, alpha |
| 331. | NFKBIA | nuclear factor of kappa light polypeptide gene enhancer in B-cells inhibitor, alpha |
| 332. | MMP13 | matrix metalloproteinase 13 (callagenase 3) |
| 333. | TSHR | thyroid stimulating hormone receptor |
| 334. | MT2A | metallothionein 2A |
| 335. | TSSC3 | tumor suppressing subtransferable candidate 3 |
| 336. | RHO | rhodopsin (opsin 2, rod pigment) (retinitis pigmentosa 4, autosomal dominant) |
| 337. | GADD45A | growth arrest and DNA-damage-inducible, alpha |
| 338. | LCAT | lecithin-cholesterol acyltransferase |
| 339. | GSR | glutathione reductase |
| 340. | TOP2A | topoisomerase (DNA) II alpha (170 kD) |
| 341. | GPX1 | glutathione peroxidase 1 |

TABLE 1-continued

List of components which are disease-related and are detectable using the kit and/or method of the present invention.

| Number | Component | Comments |
|---|---|---|
| 342. | FLT3 | fms-related tyrosine kinase 3 |
| 343. | CEBPB | CCAAT/enhancer binding protein (C/EBP), beta |
| 344. | TPM1 | tropomyosin 1 (alpha) |
| 345. | ABCA4 | ATP-binding cassette, sub-family A (ABC1), member 4 |
| 346. | KCNH2 | potassium voltage-gated channel, subfamily H (eag-related), member 2 |
| 347. | HNF4A | hepatocyte nuclear factor 4, alpha |
| 348. | DPYD | dihydropyrimidine dehydrogenase |
| 349. | MADH2 | MAD, mothers against decapentaplegic homolog 2 (*Drosophila*) |
| 350. | AFP | alpha-fetoprotein |
| 351. | TIMP2 | tissue inhibitor of metalloproteinase 2 |
| 352. | ITK | IL2-inducible T-cell kinase |
| 353. | ABL2 | v-abl Abelson murine leukemia viral oncogene homolog 2 (arg, Abelson-related gene) |
| 354. | SCYA4 | small inducible cytokine A4 |
| 355. | GCGR | glucagon receptor |
| 356. | TCF3 | transcription factor 3 (E2A immunoglobulin enhancer binding factors E12/E47) |
| 357. | MYB | v-myb myeloblastosis viral oncogene homolog (avian) |
| 358. | LTA | lymphotoxin alpha (TNF superfamily, member 1) |
| 359. | LIF | leukemia inhibitory factor (cholinergic differentiation factor) |
| 360. | CYBB | cytochrome b-245, beta polypeptide (chronic granulomatous disease) |
| 361. | CTSL | cathepsin L |
| 362. | BCL2A1 | BCL2-related protein A1 |
| 363. | TFRC | transferrin receptor (p90, CD71) |
| 364. | RALGDS | ral guanine nucleotide dissociation stimulator |
| 365. | CYP2C8 | cytochrome P450, subfamily IIC (mephenytoin 4-hydroxylase), polypeptide 8 |
| 366. | CD38 | CD38 antigen (p45) |
| 367. | PRKCZ | protein kinase C, zeta |
| 368. | LAMR1 | laminin receptor 1 (67 kD, ribosomal protein SA) |
| 369. | IL12A | interleukin 12A (natural killer cell stimulatory factor 1, cytotoxic lymphocyte maturation factor 1, p35) |
| 370. | FGA | fibrinogen, A alpha polypeptide |
| 371. | EEF1A1 | eukaryotic translation elongation factor 1 alpha 1 |
| 372. | CYP21A2 | cytochrome P450, subfamily XXIA (steroid 21-hydroxylase, congenital adrenal hyperplasia), polypeptide 2 |
| 373. | CSF2 | colony stimulating factor 2 (granulocyte-macrophage) |
| 374. | TNFRSF5 | tumor necrosis factor receptor superfamily, member 5 |
| 375. | MBP | myelin basic protein |
| 376. | PTK2 | PTK2 protein tyrosine kinase 2 |
| 377. | KLK3 | kallikrein 3, (prostate specific antigen) |
| 378. | GALT | galactose-1-phosphate uridylyltransferase |
| 379. | APEX | APEX nuclease (multifunctional DNA repair enzyme) |
| 380. | EPHB2 | EphB2 |
| 381. | BIK | BCL2-interacting killer (apoptosis-inducing) |
| 382. | SLC2A1 | solute carrier family 2 (facilitated glucose transporter), member 1 |
| 383. | IL2RA | interleukin 2 receptor, alpha |
| 384. | IFNGR2 | interferon gamma receptor 2 (interferon gamma transducer 1) |
| 385. | AXL | AXL receptor tyrosine kinase |
| 386. | ADRB1 | adrenergic, beta-1-, receptor |
| 387. | RAD51 | RAD51 homolog (RecA homolog, *E. coli*) (*S. cerevisiae*) |
| 388. | GJA1 | gap junction protein, alpha 1, 43 kD (connexin 43) |
| 389. | EWSR1 | Ewing sarcoma breakpoint region 1 |
| 390. | CCR2 | chemokine (C—C motif) receptor 2 |
| 391. | RELA | v-rel reticuloendotheliosis viral oncogene homolog A, nuclear factor of kappa light polypeptide gene enhancer in B-cells 3, p65 (avian) |
| 392. | CTNNA1 | catenin (cadherin-associated protein), alpha 1 (102 kD) |
| 393. | MYO7A | myosin VIIA (Usher syndrome 1B (autosomal recessive, severe)) |
| 394. | F3 | coagulation factor III (thromboplastin, tissue factor) |
| 395. | EPHX1 | epoxide hydrolase 1, microsomal (xenobiotic) |
| 396. | CRK | v-crk sarcoma virus CT10 oncogene homolog (avian) |
| 397. | ENO1 | enolase 1, (alpha) |
| 398. | TGFBR1 | transforming growth factor, beta receptor I (activin A receptor type II-like kinase, 53 kD) |
| 399. | RAC1 | ras-related C3 botulinum toxin substrate 1 (rho family, small GTP binding protein Rac1) |

TABLE 1-continued

List of components which are disease-related and are detectable using the kit and/or method of the present invention.

| Number | Component | Comments |
|---|---|---|
| 400. | ANPEP | alanyl (membrane) aminopeptidase (aminopeptidase N, aminopeptidase M, microsomal aminopeptidase, CD13, p150) |

A kit and/or method according to the invention may be used to detect infectious diseases. Some infectious diseases are life threatening and can appear in combination with other infections. Thus, the sooner they can be detected and characterised, the sooner an appropriate therapy can be established and better for the patient. A kit and/or method as disclosed above can be used to detect said infectious agents. Components which may be detected according to the kit and/or method are those which form part of the infectious agent and/or are produced by the infectious agent. Viruses in diseased individuals detectable according to the kit and/or method include, but are not limited to HCV, HIV, HBV, HTLV, HPV (see also oncology). Bacteria in diseased individuals detectable according to the kit and/or method include, but are not limited to mycobacteria, syphilis, *Staphylococcus aureus* (screening of MRSA).

A kit and/or method according to the invention may be used to detect neurodegenerative diseases. Components which may be detected are those involved in degenerative diseases and include, but are not limited to beta-amyloids (Alzheimer's disease), hTAU, phosphoTAU and APOE.

A kit and/or method according to the invention may be used to detect prion-related diseases. Diseases associated with prions include Kreutzfeld Jacob disease and BSE.

A kit and/or method according to the invention may be used to detect diseases related to autoimmunity. Components which may be detected are those involved in autoimmunity include, but are not limited to ANA, Jo-1, Myeloperoxidase, RNP, Scl-70, Sm, SS-A.

A kit and/or method according to the invention may be used to detect diseases related to allergy. Components which may be detected are those involved in allergy and include, but are not limited to IgE, IgG-subclasses and circulating antibodies.

A kit and/or method according to the invention may be used in the field of genomics to detect susceptibility to disease, possibility of passing conditions to offspring, single nucleotide polymorphisms etc. Examples of fields in which a kit and/or method of the invention apply include, but are not limited to HLA typing, p53 polymorphism (SNP) related to the sensitivity of developing a cervix carcinoma after an HPV 16 infection, hypertension, detection of polymorphism in relation to the susceptibility for osteoporosis, detection of mutations in Factor V (Leiden), detection of the genetic susceptibility for SIDS (cot death), hereditary: paternity tests, etc., detection of micro satellite instability, detection of the success rate of therapy related to cessation of smoking, detection of disturbances in the metabolism of lipids including cholesterol (HDL, LDL, VLDL and their receptors) in relationship to cardiovascular diseases such as atheromathosis, detection of genomic defects related to obesitas, detection of genomic defects related to diabetes, detection of mutations associated with drug resistance (to HIV, etc.), screening and detection of systic fibrosis (CFTR mutations), detection of mutations in the mitochondrial genome related to a number of diseases as: neurogenic muscular weakness, retinitis pigmentosa, ocular myopathy, etc.

A kit and/or method according to the invention may be used in the fields related to environmental testing. Many applications are related to water where it is important to have a technology which is sensitive enough to detect very small amounts of contaminants or unwanted compounds in reasonably economical manner. Examples of environmental tests include:

checking (monitoring) of yeast infections in swimming pool water monitoring of biological pollution in general biological contaminants in potable water (amoebae, coliform bacteria, etc.).

In addition to water testing, the environmental testing for genetically modified organisms may be performed according to a kit and/or method of the present invention. Genetically Modified Organisms can be detected, or samples screened for the absence of. Checking for possible modifications is sometimes difficult, however, a sensitive technique such as that provided by the present method is suitable for such a purpose.

A kit and/or method according to the invention may be used to detect the infection of food. Inspection of all places and objects related to food needs sensitive methods, and kit and/or method of the present invention provide the required sensitivity. Furthermore, a kit and/or method of the present invention can be performed and the results obtained at the site at which the inspection takes place, so obviating the need to send samples to a lab. Thus, steps can be taken immediately if necessary. Examples of the agents that may be detected include *Listeria, Salmonella*, prions (for BSE). Molecules which may be detected assay are those which form part of the agent and/or are produced by the agent.

A kit and/or method of the present invention may be applied in standard biochemical detection protocols. All the existing types of blotting techniques show an enhancement in sensitivity using the method disclosed herein, without the requirement for radioisotopes or chemilluminescent detection such as photographic plates, or phosphor screens. It is also possible to use the method in combination with image analysis. Examples of blotting protocols that may use methods of the present invention include but are not limited to Western blotting, Northern blotting, Southern blotting, vacuum blotting, contact blotting, reversed line blot and related techniques, dot blotting, micro-arrays, macro-arrays.

Another embodiment of the present invention is a method for staining sections of cells and/or tissues suitable for visualisation using microscopy. Types of microscopy may be any, and include, but are not limited to light microscopy, tunneling electron microscopy, scanning electron microscopy, transmission electron microscopy.

According to one aspect of the invention, a method for staining components in cell and/or tissue sections, said staining suitable for visualisation using microscopy comprises the following steps:

n) incubating section with one or more tagged probes directed against a component, m) incubating section with metal-particle-labeled anti-tag monoclonal or polyclonal antibody, said antibody raised in species A, o) incubating section with an antibody conjugate, said conjugate comprising:
  one or more antibodies, anti-A, directed against immunoglobulins of species A,
  one or more antibodies, anti-B, directed against immunoglobulins of species B, optionally one or more substances which directly or indirectly cause a quantitative colour change, p) incubating the section with a polypeptide capable recognition by anti-B antibodies, said polypeptide labelled with one or more substances which directly or indirectly cause a quantitative colour change, and q) optionally incubating the section in a metal enhancement reagent and/or a colour change reagent that is a suitable substrate of an enzyme attached to the antibody conjugate.

The antibody conjugate is already defined herein. The introduction of other steps into the method, such as wash steps, for example, may be known by the skilled artisan practicing in the field of immunohistochemistry. The "metal enhancement reagent" of step q) is already defined herein for step i). The sections described above are visualised by observing the dye, by observing the metal, by metal enhancement and/or by making use of the enzyme that catalyses the colour change attached to the antibody conjugate. It is an aspect of the invention to visualise the samples using metal enhancement alone. It is an aspect of the invention to visualise the samples by observing the dye alone. It is an aspect of the invention to visualise the samples by observing the metal without metal enhancement. It is an aspect of the invention to visualise the samples using only enzyme-linked colour change. It is an aspect of the invention to visualise the samples using one or more of the aforementioned visualisations.

In another aspect of the invention, the use of tagged probe as described in a method above is circumvented by using an antibody raised in species A directly against a component in the section. Thus, in this embodiment of the invention, step n) as described above is absent, and step m) reads:

m) incubating section with metal-particle labeled anti-component monoclonal or polyclonal antibodies, said antibodies raised in species A.

Another embodiment of the present invention is a method for detecting a component in a section, said method as describe above, further comprising, after step p) the steps of:

p-1) repeating steps o) to p), and p-2) optionally repeating step p-1).

The steps described in the embodiment above are an amplification, which further enhances the sensitivity of the above method, while minimizing the increase in background signal.

Another embodiment of the present invention is a kit for staining sections of cells and/or tissues suitable for visualisation using microscopy comprising the following components:

q) a container in which a quantity of antibody conjugate as described above is present.

A container may be any sealed or resealable vessel as described elsewhere herein.

A kit for staining sections according to the present invention allows a skilled artisan to perform one or more steps of the method disclosed herein, in a convenient manner. The kit may allow a method of the present invention to be performed without the need to measure or determine the concentrations of reagents, so enabling a fast and reproducible staining of sections.

Another aspect of the present invention is a kit for staining sections as disclosed herein, further comprising one or more metal-particle-labelled probes. Each probe may be specific for a component in a section to be detected.

Another aspect of the present invention is a kit as disclosed herein, comprising antibody conjugate.

Another aspect of the present invention is a kit as disclosed herein, anti-tag antibody raised in species A, said antibody optionally labeled with metal particle.

Another aspect of the present invention is a kit as disclosed herein comprising one or more additional containers in which reagent necessary for visualisation using the colour change enzyme linked to the antibody conjugate are present.

Another aspect of the present invention is a kit as disclosed herein comprising one or more additional containers in which reagent necessary for performing metal enhancement are present.

Another aspect of the present invention is a kit as disclosed herein, a polypeptide capable recognition by anti-B antibodies, said polypeptide labelled with one or more substances which directly or indirectly cause a quantitative colour change.

Another aspect of the invention is a kit as disclosed herein comprising one or more additional containers in which metal-particle-labelled anti-component antibodies are present.

Another aspect of the invention is a kit as disclosed herein comprising one or more additional containers in which a tagged probe(s) capable of binding to a component(s) is present.

Another aspect of the invention is a kit as disclosed herein comprising one or more additional containers in which a polypeptide capable recognition by anti-B antibodies, said polypeptide labelled with one or more substances which directly or indirectly cause a quantitative colour change is present In another aspect of the invention, the kit for staining sections enables the skilled person to perform one or more of the method disclosed herein. The kit may comprise one or more additional containers in which reagents are present enabling the skilled person to perform the complete method. Alternatively, the kit may comprise a minimum number of containers, such as only item q), for example, that enables a skilled person to perform the method disclosed herein.

In another aspect of the invention, the kit contains instructions for use. In another aspect of the invention the instructions describe a method of the invention as disclosed herein.

A method and/or kit of the present invention for staining sections of cells may equally well be performed on any cell or tissue in the applications of flow cytometry and in situ hybridisation, wherein the visualisation of cells and tissues is necessary. Due to the sensitivity of the method as disclosed herein, target antigens (proteins and other substances) can be visualised in tissues and cells with antibodies and, using in situ hybridization, they can be visualised by use of nucleic acid probes.

EXAMPLES

Section 1: Materials and Methods

Oligonucleotides

```
Target:          5' GGATTATTGTTAAATATTGATAAGGAT 3'

Visualisation    5' ATCCTTATCAATATT 3'
oligo:

Oligo op drager: 5' TAACAATAATCC 3'
```

The above mentioned oligonucleotides are derived from the Anthrax lethal factor genome.

Nylon or Nitrocellulose Coated Slides

Coated slides such as Nytran coated slides, nitrocellulose coated slides were purchased from Schleicher and Schuell and printed with DNA capturing oligonucleotides using a Microcast micro-arrayer.

Mofified DNA oligonucleotides were custom made by Qbiogene (France) and in varying concentrations dissolved in printing buffer (6×SSC).

Micro-arrays were manufactured by printing varying oligonucleotide concentrations ranging from 0.001 μM to 20 μM on the coated glass slide. Negative controls consisted of printing buffer without DNA oligonucleotides and printing buffer with a DNA oligonucleotide complementary to a non-related sequence in the same concentration as the capturing oligonucleotide of interest. After drying during 30 minutes at room temperature, the slides were baked at 80° C. during 30 minutes. DNA printed at Nytran coated slides was cross linked using UV radiation according to previously described protocols.

Slides were stored dustfree at 4° C. until further analysis.

Silane Coated Slides

Coated slides such as Nytran coated slides, nitrocellulose coated slides were purchased from Schleicher and Schuell and printed with DNA oligonucleotides using a Microcast micro-arrayer.

DNA oligonucleotides were custom made by Qbiogene (France) and in varying concentrations dissolved in printing buffer. Silane coated slides and modified oligonucleotides were activated according to previously described protocols.

Micro-arrays were manufactured by printing varying oligonucleotide concentrations ranging from 0.001 μM to 20 μM on the activated silane coated glass slide. After drying during 30 minutes at room temperature, the printed slides were stored dustfree at 4° C.

Classical Glass Slides

Classical microscopical glass slides were washed with bidistilled water followed by immersion in a 10% NaOH solution at room temperature after an ultrasound treatment during 30 minutes. After several washes in running tap water, slides were washed several times with bidistilled water. Afterwards the slides were dried at 80° C.

Modified oligonucleotides were activated and coupled with aminosilane according to previously described protocols (Kumar et al. Silanized nucleic acids: a general platform for DNA immobilization. Nucleic acids res 2000; 28: e71.).

The silanized oligonucleotides were dissolved in printing buffer (50% DMSO,) and printed as described above.

Printing of the Micro-Arrays

Micro-arrays were printed with each concentration in sixfold, capturing oligonucleotides as well as the above described appropriate negative controls.

Section 2: Experiments to Compare Methods of Detection Using Gold and Enzyme Visualisations in Combination with Polymer Amplification and Other Technologies Part 1—Visualization Experiments of Labeled Oligonucleotides Attached at the Above Described Solid Assays Experiment 1—part 1: Visualization of Labeled Oligonucleotides using Streptavidin Micro-arrays were printed as described previously. All concentrations ranging from 0.001 μM to 20 μM were spotted in sixfold. Micro-arrays were baked at 80° C. during 30 minutes and stored dust-free at 4° C. until use.

Slides were washed twice with PBS (pH 7.4) supplemented with BSA (SERVA, Germany).

Slides were incubated with the same PBS/BSA buffer solution during 30 minutes at room temperature.

Slides were incubated with streptavidin/alkaline phosphatase (concentration 1/1000 in PBS/BSA buffer) (Roche Germany) during 60 minutes followed by three washes with PBS/BSA buffer at room temperature.

The alkaline phosphatase reaction was developed by incubating the slides with napthol substrate in appropriate buffer (Dako, Denmark) during 30 minutes at room temperature.

Experiment 2—Part 1: Visualization of Labeled Oligonucleotides using Streptavin Labeled with Gold Particles Micro-arrays were printed like described previously. All concentrations ranging from 0.001 μM to 20 μM were spotted in sixfold. Micro-arrays were baked at 80° C. during 30 minutes and stored dust-free at 4° C. until use.

Slides were washed twice with PBS (pH 7.4) supplemented with BSA.

Slides were incubated with the same PBS/BSA buffer solution for 30 minutes at room temperature.

Slides were washed twice with special washing buffer (PBS pH 7.4 supplemented with BSA for 5 minutes.

Slides were incubated with streptavidin/gold 0.8 nm (concentration 1/50 in washing buffer) or 6 nm (concentration 1/20 in washing buffer) (Aurion, the Netherlands) for 120 minutes followed by six washes with washing buffer at room temperature.

Slides were rinsed triplefold for five minutes with PBS, followed by distilled water.

The gold particles were visualized by silver enhancement (Aurion, the Netherlands) for 15 minutes.

Experiment 3—Part 1: Visualization of Labeled Oligonucleotides using Monoclonal Antibodies Labeled with Gold Particles Micro-arrays were printed like described previously. All concentrations ranging from 0.001 μM to 20 μM were spotted in sixfold. Micro-arrays were baked at 80° C. during 30 minutes and stored dust-free at 4° C. until use.

Slides were washed twice with PBS (pH 7.4) supplemented with BSA.

Slides were incubated with the same PBS/BSA buffer solution for 30 minutes at room temperature.

Slides were washed twice with special washing buffer (PBS pH 7.4 supplemented with BSA) for 5 minutes.

Slides were incubated with monoclonal antibody/gold 0.8 nm (concentration 1/50 in washing buffer), 6 nm (concentration 1/20 in washing buffer) or 40 nm during 120 minutes followed by six washes with washing buffer at room temperature.

Slides were rinsed triplefold during five minutes with PBS, followed by distilled water.

The gold particles were visualized by silver enhancement during 15 minutes.

Experiment 4—Part 1: Visualization of Labeled Oligonucleotides using Polyclonal Antibodies Labeled with Gold Particles Micro-arrays were printed like described previously. All concentrations ranging from 0.001 μM to 20 μM were spotted in sixfold. Micro-arrays were baked at 80° C. during 30 minutes and stored dust-free at 4° C. until use.

Slides were washed twice with PBS (pH 7.4) supplemented with BSA.

Slides were incubated with the same PBS/BSA buffer solution during 30 minutes at room temperature.

Slides were washed twice with special washing buffer (PBS pH 7.4 supplemented with BSA) during 5 minutes.

Slides were incubated with monoclonal antibody/gold 0.8 nm (concentration 1/50 in washing buffer) or 6 nm (concentration 1/20 in washing buffer) during 120 minutes followed by six washes with washing buffer at room temperature.

Slides were rinsed triplefold during five minutes with PBS, followed by distilled water.

The gold particles were visualized by silver enhancement during 15 minutes.

Experiment 5—Part 1: Visualization of Labeled Oligonucleotides using Monoclonal and Polyclonal Antibodies in a Polymer Enhanced Amplification Technique Visualized Enzymatically Micro-arrays were printed like described previously. All concentrations ranging from 0.001 μM to 20 μM were spotted in sixfold. Micro-arrays were baked at 80° C. during 30 minutes and stored dust-free at 4° C. until use.

Slides were washed twice with PBS (pH 7.4) supplemented with BSA.

Slides were incubated with the same PBS/BSA buffer solution during 30 minutes at room temperature.

Slides were washed twice with special washing buffer (PBS pH 7.4 supplemented with BSA) during 5 minutes and incubated with the same washing buffer.

Slides were incubated with monoclonal or polyclonal antibody labeled with gold particles ranging from 0.6 nm to 40 nm during 60 minutes followed by six washes with washing buffer at room temperature.

Slides were incubated with dextran polymer coated with numerous anti-mouse antibodies and anti-rabbit antibodies and labeled with alkaline phosphatase enzym for 30 minutes followed by six washes with washing buffer.

The alkaline phosphatase reaction was developed by incubating the slides with napthol substrate in appropriate buffer during 30 minutes at room temperature.

Experiment 6—Part 1: Visualization of Labeled Oligonucleotides using Gold Labeled Monoclonal and Polyclonal Antibodies in a Polymer Enhanced Amplification Technique Micro-arrays were printed like described previously. All concentrations ranging from 0.001 μM to 20 μM were spotted in sixfold. Micro-arrays were baked at 80° C. during 30 minutes and stored dust-free at 4° C. until use.

Slides were washed twice with PBS (pH 7.4) supplemented with BSA.

Slides were incubated with the same PBS/BSA buffer solution during 30 minutes at room temperature.

Slides were washed twice with special washing buffer (PBS pH 7.4 supplemented with BSA) during 5 minutes and incubated with the same washing buffer.

Slides were incubated with monoclonal or polyclonal antibody labeled with gold particles ranging from 0.6 nm to 40 nm during 60 minutes followed by six washes with washing buffer at room temperature.

Slides were incubated with dextran polymer coated with numerous anti-mouse antibodies and anti-rabbit antibodies for 30 minutes followed by six washes with washing buffer.

Slides were incubated with monoclonal or polyclonal antibody labeled with gold particles ranging from 0.6 nm to 40 nm during 60 minutes followed by six washes with washing buffer at room temperature Slides were rinsed triplefold during five minutes with PBS, followed by distilled water.

The gold particles were visualized by silver enhancement during 15 minutes.

Experiment 7—Part 1: Visualization of Labeled Oligonucleotides using CARD Amplification Technology Visualized Enzymatically Micro-arrays were printed like described previously. All concentrations ranging from 0.001 μM to 20 μM were spotted in sixfold. Micro-arrays were baked at 80° C. during 30 minutes and stored dust-free at 4° C. until use.

Slides were washed twice with PBS (pH 7.4) supplemented with BSA.

Slides were incubated with the same PBS/BSA buffer solution during 30 minutes at room temperature.

Slides were incubated with streptavidin/peroxidases (concentration 1/500 in PBS/BSA buffer) during 60 minutes followed by three washes with PBS/BSA buffer at room temperature.

The slide was incubated with biotinylated tyramine diluted 1/50 in PBS solution supplemented with 0.03% $H_2O_2$ for 10 minutes followed by three washes with wash buffer during 5 minutes.

Slides were incubated with streptavidin/alkaline phosphatase (concentration 1/1000 in PBS/BSA buffer) during 60 minutes followed by three washes with PBS/BSA buffer at room temperature.

The alkaline phosphatase reaction was developed by incubating the slides with napthol substrate in appropriate buffer during 30 minutes at room temperature.

Experiment 8—Part 1: Visualization of Labeled Oligonucleotides using CARD Amplification Technology Visualized with Gold Labeled Streptavidin Micro-arrays were printed like described previously. All concentrations ranging from 0.001 μM to 20 μM were spotted in sixfold. Micro-arrays were baked at 80° C. during 30 minutes and stored dust-free at 4° C. until use.

Slides were washed twice with PBS (pH 7.4) supplemented with BSA.

Slides were incubated with the same PBS/BSA buffer solution during 30 minutes at room temperature.

Slides were incubated with streptavidin/peroxidases (concentration 1/500 in PBS/BSA buffer) during 60 minutes followed by three washes with PBS/BSA buffer at room temperature.

The slide was incubated with biotinylated tyramine diluted 1/50 in PBS solution supplemented with 0.03% $H_2O_2$ for 10 minutes followed by three washes with wash buffer during 5 minutes.

Slides were incubated with streptavidin/gold 0.8 nm (concentration 1/50 in washing buffer) or 6 nm (concentration 1/20 in washing buffer) during 120 minutes followed by six washes with washing buffer at room temperature.

Slides were rinsed triplefold during five minutes with PBS, followed by distilled water.

The gold particles were visualized by silver enhancement during 15 minutes.

Experiment 9—Part 1: Visualization of Labeled Oligonucleotides using CARD Amplification Technology Visualized with Gold Labeled Monoclonal or Polyclonal Antibodies Micro-arrays were printed like described previously. All concentrations ranging from 0.001 µM to 20 µM were spotted in sixfold. Micro-arrays were baked at 80° C. during 30 minutes and stored dust-free at 4° C. until use.

Slides were washed twice with PBS (pH 7.4) supplemented with BSA.

Slides were incubated with the same PBS/BSA buffer solution during 30 minutes at room temperature.

Slides were incubated with streptavidin/peroxidases (concentration 1/500 in PBS/BSA buffer) during 60 minutes followed by three washes with PBS/BSA buffer at room temperature.

The slide was incubated with biotinylated tyramine diluted 1/50 in PBS solution supplemented with 0.03% $H_2O_2$ for 10 minutes followed by three washes with wash buffer during 5 minutes.

Slides were washed twice with special washing buffer (PBS pH 7.4 supplemented with BSA) during 5 minutes.

Slides were incubated with monoclonal or polyclonal antibody labeled with gold particles ranging from 0.6 nm to 40 nm during 120 minutes followed by six washes with washingbuffer at room temperature.

Slides were rinsed triplefold during five minutes with PBS, followed by distilled water.

The gold particles were visualized by silver enhancement during 15 minutes.

Part 2: Hybridization Experiments of Labeled Oligonucleotides Attached at the Above Described Solid Assays Experiment 2.1—Part 2: Visualization of Labeled Oligonucleotides using Streptavidin Micro-arrays were printed like described previously. All concentrations ranging from 0.001 µM to 20 µM were spotted in sixfold including adequate positive and negative controls. Micro-arrays were baked at 80° C. during 30 minutes and stored dust free at 4° C. until use.

The slides were prehybridized with hybridization mixture supplemented with sonicated herring sperm DNA (150 µg/5 ml hybridization mixture) for 2 hours at room temperature.

Hybridization assay was set up using target DNA and/or visualisation oligonucleotide in a concentration of 250 ng/ml hybridization mixture. Hybridization was carried out overnight at 37° C.

Slides were washed twice with 2×SSC at room temperature.

Slides were washed twice with PBS (pH 7.4) supplemented with BSA.

Slides were incubated with the same PBS/BSA buffer solution during 30 minutes at room temperature.

Slides were incubated with streptavidin/alkaline phosphatase (concentration 1/1000 in PBS/BSA buffer) during 60 minutes followed by three washes with PBS/BSA buffer at room temperature.

The alkaline phosphatase reaction was developed by incubating the slides with napthol substrate in appropriate buffer during 30 minutes at room temperature.

Experiment 2.2—Part 2: Visualization of Labeled Oligonucleotides using Streptavin Labeled with Gold Particles Micro-arrays were printed like described previously. All concentrations ranging from 0.001 µM to 20 µM were spotted in sixfold. Micro-arrays were baked at 80° C. during 30 minutes and stored dust-free at 4° C. until use.

The slides were prehybridized with hybridization mixture supplemented with sonicated herring sperm DNA (150 µg/5 ml hybridization mixture) for 2 hours at room temperature.

Hybridization assay was set up using target DNA and/or visualisation oligonucleotide consisting of labeled oligonucleotide in a concentration of 250 ng/ml hybridization mixture.

Hybridization was carried out overnight at 37° C.

Slides were washed twice with 2×SSC at room temperature.

Slides were washed twice with PBS (pH 7.4) supplemented with BSA.

Slides were incubated with the same PBS/BSA buffer solution during 30 minutes at room temperature.

Slides were washed twice with special washing buffer (PBS pH 7.4 supplemented with BSA) during 5 minutes.

Slides were incubated with streptavidin/gold 0.8 nm (concentration 1/50 in washing buffer) or 6 nm (concentration 1/20 in washing buffer) during 120 minutes followed by six washes with washing buffer at room temperature.

Slides were rinsed triplefold during five minutes with PBS, followed by distilled water.

The gold particles were visualized by silver enhancement during 15 minutes.

Experiment 3—Part 2: Visualization of Labeled Oligonucleotides using Monoclonal Antibodies Labeled with Gold Particles Micro-arrays were printed like described previously. All concentrations ranging from 0.001 µM to 20 µM were spotted in sixfold. Micro-arrays were baked at 80° C. during 30 minutes and stored dustfree at 4° C. until use.

The slides were prehybridized with hybridization mixture supplemented with sonicated herring sperm DNA (150 µg/5 ml hybridization mixture) for 2 hours at room temperature.

Hybridization assay was set up using target DNA and/or visualisation oligonucleotide consisting of labeled oligonucleotide in a concentration of 250 ng/ml hybridization mixture.

Hybridization was carried out overnight at 37° C.

Slides were washed twice with 2×SSC at room temperature

Slides were washed twice with PBS (pH 7.4) supplemented with BSA.

Slides were incubated with the same PBS/BSA buffer solution during 30 minutes at room temperature.

Slides were washed twice with special washing buffer (PBS pH 7.4 supplemented with BSA) during 5 minutes.

Slides were incubated with monoclonal antibody/gold 0.8 nm (concentration 1/50 in washing buffer) or 6 nm (concentration 1/20 in washing buffer), or 40 nm for 120 minutes followed by six washes with washing buffer at room temperature.

Slides were rinsed triplefold during five minutes with PBS, followed by distilled water.

The gold particles were visualized by silver enhancement during 15 minutes.

Experiment 4—Part 2: Visualization of Labeled Oligonucleotides using Polyclonal Antibodies Labeled with Gold Particles Micro-arrays were printed like described previously. All concentrations ranging from 0.001 µM to 20 µM were spotted in sixfold. Micro-arrays were baked at 80° C. during 30 minutes and stored dust-free at 4° C. until use.

The slides were prehybridized with hybridization mixture supplemented with sonicated herring sperm DNA (150 µg/5 ml hybridization mixture) for 2 hours at room temperature.

Hybridization assay was set up using target DNA and/or visualisation oligonucleotide consisting of labeled oligonucleotide in a concentration of 250 ng/ml hybridization mixture.

Hybridization was carried out overnight at 37° C.

Slides were washed twice with 2×SSC at room temperature

Slides were washed twice with PBS (pH 7.4) supplemented with BSA.

Slides were incubated with the same PBS/BSA buffer solution during 30 minutes at room temperature.

Slides were washed twice with special washing buffer (PBS pH 7.4 supplemented with BSA) during 5 minutes.

Slides were incubated with monoclonal antibody/gold 0.8 nm (concentration 1/50 in washing buffer) or 6 nm (concentration 1/20 in washing buffer) during 120 minutes followed by six washes with washing buffer at room temperature.

Slides were rinsed triplefold during five minutes with PBS, followed by distilled water.

The gold particles were visualized by silver enhancement during 15 minutes.

Experiment 5—Part 2: Visualization of Labeled Oligonucleotides using Monoclonal and Polyclonal Antibodies in a Polymer Enhanced Amplification Technique Visualized Enzymatically Micro-arrays were printed like described previously. All concentrations ranging from 0.001 µM to 20 µM were spotted in sixfold. Micro-arrays were baked at 80° C. during 30 minutes and stored dust-free at 4° C. until use.

The slides were prehybridized with hybridization mixture supplemented with sonicated herring sperm DNA (150 µg/5 ml hybridization mixture) for 2 hours at room temperature.

Hybridization assay was set up using target DNA and/or visualisation oligonucleotide consisting of labeled oligonucleotide in a concentration of 250 ng/ml hybridization mixture.

Hybridization was carried out overnight at 37° C.

Slides were washed twice with 2×SSC at room temperature

Slides were washed twice with PBS (pH 7.4) supplemented with BSA.

Slides were incubated with the same PBS/BSA buffer solution during 30 minutes at room temperature.

Slides were washed twice with special washing buffer (PBS pH 7.4 supplemented with BSA) during 5 minutes and incubated with the same washing buffer.

Slides were incubated with monoclonal or polyclonal antibody labeled with gold particles ranging from 0.6 nm to 40 nm during 60 minutes followed by six washes with washing buffer at room temperature.

Slides were incubated with dextran polymer coated with numerous anti-mouse antibodies and anti-rabbit antibodies and labeled with alkaline phosphatase enzyme for 30 minutes followed by six washes with washing buffer.

The alkaline phosphatase reaction was developed by incubating the slides with napthol substrate in appropriate buffer during 30 minutes at room temperature.

Experiment 6—Part 2: Visualization of Labeled Oligonucleotides using Gold Labeled Monoclonal and Polyclonal Antibodies in a Polymer Enhanced Amplification Technique Micro-arrays were printed like described previously. All concentrations ranging from 0.001 µM to 20 µM were spotted in sixfold. Micro-arrays were baked at 80° C. during 30 minutes and stored dust-free at 4° C. until use.

The slides were prehybridized with hybridization mixture supplemented with sonicated herring sperm DNA (150 µg/5 ml hybridization mixture) for 2 hours at room temperature.

Hybridization assay was set up using target DNA and/or visualisation oligonucleotide consisting of labeled oligonucleotide in a concentration of 250 ng/ml hybridization mixture.

Hybridization was carried out overnight at 37° C.

Slides were washed twice with 2×SSC at room temperature

Slides were washed twice with PBS (pH 7.4) supplemented with BSA.

Slides were incubated with the same PBS/BSA buffer solution during 30 minutes at room temperature.

Slides were washed twice with special washing buffer (PBS pH 7.4 supplemented with BSA) during 5 minutes and incubated with the same washing buffer.

Slides were incubated with monoclonal or polyclonal antibody labeled with gold particles ranging from 0.6 nm to 40 nm during 60 minutes followed by six washes with washing buffer at room temperature.

Slides were incubated with dextran polymer coated with numerous anti-mouse antibodies and anti-rabbit antibodies for 30 minutes followed by six washes with washing buffer.

Slides were incubated with monoclonal or polyclonal antibody labeled with gold particles ranging from 0.6 nm to 40 nm during 60 minutes followed by six washes with washing buffer at room temperature Slides were rinsed triplefold during five minutes with PBS, followed by distilled water.

The gold particles were visualized by silver enhancement during 15 minutes.

Experiment 7—Part 2: Visualization of Labeled Oligonucleotides using CARD Amplification Technology Visualized Enzymatically Micro-arrays were printed like described previously. All concentrations ranging from 0.001 µM to 20 µM were spotted in sixfold. Micro-arrays were baked at 80° C. during 30 minutes and stored dust-free at 4° C. until use.

The slides were prehybridized with hybridization mixture supplemented with sonicated herring sperm DNA (150 µg/5 ml hybridization mixture) for 2 hours at room temperature.

Hybridization assay was set up using target DNA and/or visualisation oligonucleotide consisting of labeled oligonucleotide in a concentration of 250 ng/ml hybridization mixture.

Hybridization was carried out overnight at 37° C.

Slides were washed twice with 2×SSC at room temperature

Slides were washed twice with PBS (pH 7.4) supplemented with BSA.

Slides were incubated with the same PBS/BSA buffer solution during 30 minutes at room temperature.

Slides were incubated with streptavidin/peroxidases (concentration 1/500 in PBS/BSA buffer) during 60 minutes followed by three washes with PBS/BSA buffer at room temperature.

The slide was incubated with biotinylated tyramine diluted 1/50 in PBS solution supplemented with 0.03% $H_2O_2$ for 10 minutes followed by three washes with wash buffer during 5 minutes.

Slides were incubated with streptavidin/alkaline phosphatase (concentration 1/1000 in PBS/BSA buffer) during 60 minutes followed by three washes with PBS/BSA buffer at room temperature.

The alkaline phosphatase reaction was developed by incubating the slides with napthol substrate in appropriate buffer during 30 minutes at room temperature.

Experiment 8—Part 2: Visualization of Labeled Oligonucleotides using CARD Amplification Technology Visualized with Gold Labeled Streptavidin Micro-arrays were printed like described previously. All concentrations ranging from 0.001 µM to 20 µM were spotted in sixfold. Micro-arrays were baked at 80° C. during 30 minutes and stored dust-free at 4° C. until use.

The slides were prehybridized with hybridization mixture supplemented with sonicated herring sperm DNA (150 µg/5 ml hybridization mixture) for 2 hours at room temperature.

Hybridization assay was set up using target DNA and/or visualisation oligonucleotide consisting of labeled oligonucleotide in a concentration of 250 ng/ml hybridization mixture.

Hybridization was carried out overnight at 37° C.

Slides were washed twice with 2×SSC at room temperature

Slides were washed twice with PBS (pH 7.4) supplemented with BSA.

Slides were incubated with the same PBS/BSA buffer solution during 30 minutes at room temperature.

Slides were incubated with streptavidin/peroxidases (concentration 1/500 in PBS/BSA buffer) during 60 minutes followed by three washes with PBS/BSA buffer at room temperature.

The slide was incubated with biotinylated tyramine diluted 1/50 in PBS solution supplemented with 0.03% $H_2O_2$ for 10 minutes followed by three washes with wash buffer during 5 minutes.

Slides were incubated with streptavidin/gold 0.8 nm (concentration 1/50 in washing buffer) or 6 nm (concentration 1/20 in washing buffer) during 120 minutes followed by six washes with washing buffer at room temperature.

Slides were rinsed triplefold during five minutes with PBS, followed by distilled water.

The gold particles were visualized by silver enhancement during 15 minutes.

Experiment 9—Part 2: Visualization of Labeled Oligonucleotides using CARD Amplification Technology Visualized with Gold Labeled Monoclonal or Polyclonal Antibodies Micro-arrays were printed like described previously. All concentrations ranging from 0.001 µM to 20 µM were spotted in sixfold. Micro-arrays were baked at 80° C. during 30 minutes and stored dust-free at 4° C. until use.

The slides were prehybridized with hybridization mixture supplemented with sonicated herring sperm DNA (150 µg/5 ml hybridization mixture) for 2 hours at room temperature.

Hybridization assay was set up using target DNA and/or visualisation oligonucleotide consisting of labeled oligonucleotide in a concentration of 250 ng/ml hybridization mixture.

Hybridization was carried out overnight at 37° C.

Slides were washed twice with 2×SSC at room temperature

Slides were washed twice with PBS (pH 7.4) supplemented with BSA.

Slides were incubated with the same PBS/BSA buffer solution during 30 minutes at room temperature.

Slides were incubated with streptavidin/peroxidases (concentration 1/500 in PBS/BSA buffer) during 60 minutes followed by three washes with PBS/BSA buffer at room temperature.

The slide was incubated with biotinylated tyramine diluted 1/50 in PBS solution supplemented with 0.03% $H_2O_2$ for 10 minutes followed by three washes with wash buffer during 5 minutes.

Slides were washed twice with special washing buffer (PBS pH 7.4 supplemented with BSA) during 5 minutes.

Slides were incubated with monoclonal or polyclonal antibody labeled with gold particles ranging from 0.6 nm to 40 nm during 120 minutes followed by six washes with washing buffer at room temperature.

Slides were rinsed triplefold during five minutes with PBS, followed by distilled water.

The gold particles were visualized by silver enhancement during 15 minutes.

Results and Discussion

Results of Experiments without Signal Amplification:

Experiment 1—Visualization with Streptavidin-Enzyme

Hybridization was visualized as deep red or dark brown spots according to the used enzyme and substrate. The spots were easy discernible at the white background of the slide. Background staining was not present. Visualization was achieved with spotted molecular probe concentration ranging from 0.2 mM to 0.02 mM.

Experiment 2—Visualization with Streptavidin Gold 0.8 nm and 6 nm

Hybridization was visualized as deep black grey spots according to the used silver enhancement. The spots were easy discernible at the white background of the slide. Background staining was not presented. Visualization was achieved with spotted molecular probe concentration ranging from 0.2 mM to 0.02 mM.

Experiment 3—Visualization with Monoclonal Mouse Antibodies with Gold 0.8 nm and 6 nm Hybridization was visualized as deep black spots according to the used silver enhancement. The spots were easy discernible at the white background of the slide. Background staining was not present. Visualization was achieved with spotted molecular probe concentration ranging from 0.2 mM to 0.002 mM. However the signal was stronger with the 6 nm gold compared to the 0.8 nm gold and sharper than with the streptavidin-gold method. In comparison with the polyclonal antibodies the signal was slightly sharper.

Experiment 3—Visualization with Monoclonal Mouse Antibodies with Gold 40 nm

Hybridization was faintly visualized as light *rosa* spots only at the highest spot concentration of 0.2 mM. Silver enhancement did not yield significant signal strenghtening. Background staining was considerable.

Experiment 4—Visualization with Polyclonal Goat Antibodies with Gold 0.8 nm and 6 nm Hybridization was visualized as deep black spots according to the used silver enhancement. The spots were easy discernible at the white background of the slide. Background staining was not present. Visualization was achieved with spotted molecular probe concentration ranging from 0.2 mM to 0.002 mM. However the signal was stronger with the 6 nm gold compared to the 0.8 nm gold and sharper than with the streptavidin-gold method.

Results of Experiments with Signal Amplification—CARD-Amplification with Short Spacer:

Experiment 7—Visualization with Streptavidin-Enzyme

Hybridization was visualized as deep red or dark brown spots according to the used enzym and substrate. The spots were easy discernible at the white background of the slide. Background staining was moderate to strong. Visualization was achieved with spotted molecular probe concentration ranging from 0.2-mM to 0.0002 mM.

Experiment 8—Visualization with Streptavidin Gold 0.8 nm and 6 nm

Hybridization was visualized as deep black grey spots according to the used silver enhancement. The spots were easy discernible at the white background of the slide. Background staining was moderate. Visualization was achieved with spotted molecular probe concentration ranging from 0.2 mM to 0.0002 mM.

Experiment 9—Visualization with Polyclonal Goat Antibodies with Gold 0.8 nm and 6 nm Hybridization was visualized as deep black spots according to the used silver enhancement strategy. The spots were easy discernible at the white background of the slide. Background staining was moderate. Visualization was achieved with spotted molecular probe concentration ranging from 0.2 mM to 0.0002 mM. However the signal was stronger with the 6 nm gold compared to the 0.8 nm gold and sharper than with the streptavidin-gold method.

Experiment 9—Visualization with Monoclonal Mouse Antibodies with Gold 0.8 nm and 6 nm Hybridization was visualized as deep black spots according to the used silver enhancement. The spots were easy discernible at the white background of the slide. Background staining was moderately present. Visualization was achieved with spotted molecular probe concentration ranging from 0.2 mM to 0.002 mM. However the signal was stronger with the 6 nm gold compared to the 0.8 nm gold and sharper than with the streptavidin-gold method. In comparison with the polyclonal antibodies the signal was slightly sharper.

Experiment 9—Visualization with Monoclonal Mouse Antibodies with Gold 40 nm

Hybridization was faintly visualized as light brown spots only at the highest spot concentration of 0.2 mM. Silver enhancement did not yield significant signal enhancement. Background staining was considerable.

Results of Experiments with Signal Amplification—CARD-Amplification with Long Spacer:

Experiment 7—Visualization with Streptavidin-Enzyme

Hybridization was visualized as deep red or dark brown spots according to the used enzyme and substrate. The spots were easy discernible at the white background of the slide. Background staining was moderate. Visualization was acieved with spotted molecular probe concentration ranging from 0.2 mM to 0.0002 mM.

Experiment 8—Visualization with Streptavidin Gold 0.8 nm and 6 nm

Hybridization was visualized as deep black grey spots according to the used silver enhancement. The spots were easy discernible at the white background of the slide. Background staining was slight. Visualization was achieved with spotted molecular probe concentration ranging from 0.2 mM to 0.0002 mM.

Experiment 9—Visualization with Polyclonal Goat Antibodies with Gold 0.8 nm and 6 nm Hybridization was visualized as deep black spots according to the used silver enhancement. The spots were easy discernible at the white background of the slide. Background staining was very slight. Visualization was achieved with spotted molecular probe concentration ranging from 0.2 mM to 0.0002 mM. However the signal was stronger with the 6 nm gold compared to the 0.8 nm gold and sharper than with the streptavidin-gold method.

Experiment 9—Visualization with Monoclonal Mouse Antibodies with Gold 0.8 nm and 6 nm Hybridization was visualized as deep black spots according to the used silver enhancement. The spots were easy discernible at the white background of the slide. Background staining was very slight. Visualization was achieved with spotted molecular probe concentration ranging from 0.2 mM to 0.002 mM. However the signal was stronger with the 6 nm gold compared to the 0.8 nm gold and sharper than with the streptavidin-gold method. In comparison with the polyclonal antibodies the signal was slightly sharper.

Experiment 9—Visualization with Monoclonal Mouse Antibodies with Gold 40 nm

Hybridization was faintly visualized as light brown spots only at the highest spot concentration of 0.2 mM. Silver enhancement did not yield significant signal strenghtening. Background staining was considerable.

Results of Experiments with Signal Amplification—Amplification using Polymertechnology:

Experiment 5—Visualization with Monoclonal Antibodies/Polymer Labeled with Alkaline Phosphatase Hybridization was visualized as deep red spots. The spots were easy discernible at the white background of the slide. Background staining was slight. Visualization was achieved with spotted molecular probe concentration ranging from 0.1 mM to 0.0001 mM.

Experiment 6—Visualization with Polyclonal Goat Antibodies with Gold 0.8 nm, 6 nm and 40 nm/Polymer/Monoclonal Mouse Antibodies 0.8 nm, 6 nm and 40 nm Hybridization was visualized as deep black spots according to the used silver enhancement. The spots were easy discernible at the white background of the slide. Background staining was very slight. Visualization was achieved with spotted molecular probe concentration ranging from 0.1 mM to 0.0001 mM. However the signal was stronger with the 0.8 nm gold compared to the 6 nm gold and sharper than with the streptavidin-enzym method. The 40 nm gold particles gave a slight *rosa* reaction barely discernible with the naked eye.

Experiment 6—Visualization with Monoclonal Mouse Antibodies 0.8 nm, 6 nm, 40 nm/Polymer/Polyclonal Goat Antibodies with Gold 0.8 nm, 6 nm and 40 nm Hybridization was visualized as deep black spots according to the used silver enhancement. The spots were easy discernible at the white background of the slide. Background staining was not present. Visualization was achieved with spotted molecular probe concentration ranging from 0.1 mM to 0.0001 mM. However the signal was stronger with the 0.8 nm gold compared to the 6 nm gold and sharper than with the streptavidin-enzyme method. The 40 nm gold particles gave a slight *rosa* reaction barely discernible with the naked eye.

Experiment 6—Visualization with Monoclonal Goat Antibodies with Gold 0.8 nm, 6 nm, 40 nm/Polymer/Monoclonal Mouse Antibodies 0.8 nm, 6 nm and 40 nm Hybridization was visualized as deep black spots according to the used silver enhancement. The spots were easy discernible at the white background of the slide. Background staining was very slight. Visualization was achieved with spotted molecular probe concentration ranging from 0.1 mM to 0.0001 mM. However the signal was stronger with the 0.8 nm gold compared to the 6 nm gold and sharper than with the streptavidin-enzym method. The 40 nm gold particles gave a slight *rosa* reaction barely discernible with the naked eye.

Experiment 6—Visualization with Monoclonal Mouse Antibodies with Gold 40 nm/Polymer/Monoclonal Mouse Antibodies with Gold 40 nm Hybridization was faintly visualized as light red spots only at the highest spot concentration of 0.2 mM. Silver enhancement did not yield significant signal strengthening. Background staining was considerable.

Section 3: Detection and Subtyping of HPV DNA

Micro-arrays were printed like described previously using specific oligonucleotides detecting HPV 16, HPV 18, HPV 31, HPV 33, HPV 35, HPV 52 and HPV 58. The oligonucleotides were dissolved in printing buffer resulting in an end concentration of 10 µM and were spotted in sixfold including adequate positive and negative controls using a Microcast micro-arrayer.

This results in a micro-array with 7 seven rows, each row consisting of six identical spots, representing the seven above described HPV types. The negative controls consisted of printing buffer without DNA and a second negative control consisted of an oligonucleotide coding for a non-related gene segment and were printed as two rows consisting of six spots where one row consisted out of printing buffer without DNA and another row consisted of non-related DNA oligonucleotide.

The positive control consisted of an equimolar mixture of the above described HPV type specific oligonucleotides printed in one row consisting of six identical spots.

After printing the micro-arrays were air dried at room temperature for 15 minutes.

Micro-arrays were baked at 80° C. during 30 minutes and stored dust-free at 4° C. until use.

Hybridization with PCR Labeled Amplification Product

Hybridization assay was set up using PCR amplified HPV DNA.

During the PCR reaction the amplification product was labeled using a biotin labeled primer.

In another experiment the PCR was set up with two unlabeled primers.

Ten microliter of the PCR amplification product was denatured with 10 µl denaturation solution (NAOH/EDTA). The denatured DNA solution was added to 2 ml of hybridization mixture. The micro-arrays were covered with a cover slip and hybridized overnight at 37° C. in a humid chamber.

Slides were washed with SSC buffer.

Slides were washed twice with PBS (pH 7.4) supplemented with BSA.

The hybridization of the biotin labeled PCR product was revealed using one of the methods described above.

Visualisation with Streptavidin-Alkaline Phosphatase

Slides were incubated with the same PBS/BSA buffer solution during 30 minutes at room temperature.

Slides were incubated with streptavidin/alkaline phosphatase (concentration 1/1000 in PBS/BSA buffer) during 60 minutes followed by three washes with PBS/BSA buffer at room temperature.

The alkaline phosphatase reaction was developed by incubating the slides with napthol substrate in appropriate buffer during 30 minutes at room temperature.

Visualisation with Streptavidin-Gold

Slides were washed twice with PBS (pH 7.4) supplemented with BSA.

Slides were incubated with the same PBS/BSA buffer solution during 30 minutes at room temperature.

Slides were washed twice with special washing buffer (PBS pH 7.4 supplemented with BSA) during 5 minutes.

Slides were incubated with streptavidin/gold 0.8 nm (concentration 1/50 in washing buffer) or 6 nm (concentration 1/20 in washing buffer) during 120 minutes followed by six washes with washing buffer at room temperature.

Slides were rinsed triplefold during five minutes with PBS, followed by distilled water.

The gold particles were visualized by silver enhancement during 15 minutes.

Visualisation with Mono- or Polyclonal Anti-Biotin Antibody

Slides were washed twice with PBS (pH 7.4) supplemented with BSA.

Slides were incubated with the same PBS/BSA buffer solution during 30 minutes at room temperature.

Slides were washed twice with special washing buffer (PBS pH 7.4 supplemented with BSA) during 5 minutes.

Slides were incubated with monoclonal or polyclonal antibody/gold 0.8 nm (concentration 1/50 in washing buffer) or 6 nm (concentration 1/20 in washing buffer) during 120 minutes followed by six washes with washing buffer at room temperature.

Slides were rinsed triplefold during five minutes with PBS, followed by distilled water.

The gold particles were visualized by silver enhancement during 15 minutes.

Visualisation using Signal Amplification with Polymer Technology

Slides were washed twice with PBS (pH 7.4) supplemented with BSA.

Slides were incubated with the same PBS/BSA buffer solution during 30 minutes at room temperature.

Slides were washed twice with special washing buffer (PBS pH 7.4 supplemented with BSA) during 5 minutes and incubated with the same washing buffer.

Slides were incubated with monoclonal or polyclonal antibody labeled with gold particles ranging from 0.6 nm to 40 nm during 60 minutes followed by six washes with washing buffer at room temperature.

Slides were incubated with dextran polymer coated with numerous anti-mouse antibodies and anti-rabbit antibodies for 30 minutes followed by six washes with washing buffer.

Slides were incubated with monoclonal or polyclonal antibody labeled with gold particles ranging from 0.6 nm to 40 nm during 60 minutes followed by six washes with washing buffer at room temperature Slides were rinsed triplefold during five minutes with PBS, followed by distilled water.

The gold particles were visualized by silver enhancement during 15 minutes.

Visualisation using Signal Amplification with CARD Technology

Slides were washed twice with PBS (pH 7.4) supplemented with BSA.

Slides were incubated with the same PBS/BSA buffer solution during 30 minutes at room temperature.

Slides were incubated with streptavidin/peroxidases (concentration 1/500 in PBS/BSA buffer) during 60 minutes followed by three washes with PBS/BSA buffer at room temperature.

The slide was incubated with biotinylated tyramine diluted 1/50 in PBS solution supplemented with 0.03% $H_2O_2$ for 10 minutes followed by three washes with washbuffer during 5 minutes.

Slides were washed twice with special washing buffer (PBS pH 7.4 supplemented with BSA) during 5 minutes.

Slides were incubated with monoclonal or polyclonal antibody labeled with gold particles ranging from 0.6 nm to 40 nm during 120 minutes followed by six washes with washing buffer at room temperature.

Slides were rinsed triplefold during five minutes with PBS, followed by distilled water.

The gold particles were visualized by silver enhancement during 15 minutes

Hybridization with Unlabeled PCR Amplification Product, Visualization using Anti-DNA Antibody, Signal Amplification with Polymer Technology and Gold.

Hybridization assay was set up using PCR amplified HPV DNA.

In this part of the experiment the PCR was set up with two unlabeled primers.

Ten microliter of the PCR amplification product was denatured with 10 μl denaturation solution (NAOH/EDTA). The denatured DNA solution was added to 2 ml of hybridization mixture. The micro-arrays were covered with a cover slip and hybridized overnight at 37° C. in a humid chamber.

Slides were washed twice with 2×SSC supplemented with 0.1% SDS at room temperature.

Slides were washed twice with PBS (pH 7.4) supplemented with BSA.

The hybridization of the unlabeled PCR product with its capture oligonucleotide at the micro-array was revealed using an anti-DNA antibody.

Slides were washed twice with PBS (pH 7.4) supplemented with BSA.

Slides were incubated with the same PBS/BSA buffer solution during 30 minutes at room temperature.

Slides were washed twice with special washing buffer (PBS pH 7.4 supplemented with BSA) during 5 minutes and incubated with the same washing buffer.

Slides were incubated with anti-DNA during 60 minutes followed by six washes with washing buffer at room temperature.

Slides were incubated with dextran polymer coated with anti-mouse antibodies and anti-rabbit antibodies for 30 minutes followed by six washes with washing buffer.

Slides were incubated with monoclonal or polyclonal antibody labeled with gold particles ranging from 0.6 nm to 40 nm during 60 minutes followed by six washes with washing buffer at room temperature Slides were rinsed triplefold during five minutes with PBS, followed by distilled water.

The gold particles were visualized by silver enhancement during 15 minutes.

Results and Discussion

Hybridized micro-arrays showed areas with very sharp black or red coloured spots in some areas depending on the used substrate. Other areas did not show any signal. Background signal was completely absent.

Hybridization was revealed as easy discernible bright spots coloured deep red when using the alkaline phophatase technique for visualization or as deep grey to black spots when using gold-silver enhancement technology. The results were easily evaluated with the naked eye. The best results were obtained with gold labeled antibodies used in a polymer amplification technique.

Negative controls did not show any sign of positivity. The positive control was strongly positive. In one experiment the presence of HPV 16 was revealed and in another experiment the presence of HPV 18 was highlighted. Cross-hybridization with other molecular probes was not noted. Samples without HPV DNA did not give a signal at the micro-array.

Section 4: Application of Immunohistochemistry: Visualization of Tissue Antigens with of Monoclonal Antibodies using Gold Labeled Monoclonal and Polyclonal Antibodies in a Polymer Enhanced Amplification Technique Sections of 5 μm were cut from paraffin embedded formalin fixed tissue of squamous lung carcinoma and adhered to poly-l-lysine coated glass slides, dried at 55° C. overnight and stored dust-free at room temperature. The sections were deparaffinized in two rinses of xylene substitute, followed by rehydratation in an descending series of alcohols down to deionized water. Slides were washed twice with PBS (pH 7.4) and incubated with anti-ema (epithelial membrane antigen) monoclonal mouse antibody (Dakopatts Denmark) according to the instructions of the manufacturer). Slides were washed twice with PBS (pH 7.4) supplemented with BSA.

Slides were incubated with the same PBS/BSA buffer solution during 30 minutes at room temperature.

Slides were washed twice with special washing buffer (PBS pH 7.4 supplemented with BSA) during 5 minutes and incubated with the same washing buffer.

Slides were incubated with monoclonal or polyclonal antibody labelled with gold particles ranging from 0.6 nm to 40 nm during 60 minutes followed by six washes with washing buffer at room temperature.

Slides were incubated with dextran polymer coated with anti-mouse antibodies and anti-rabbit antibodies for 30 minutes followed by six washes with washing buffer.

Slides were incubated with monoclonal or polyclonal antibody labelled with gold particles ranging from 0.6 nm to 40 nm during 60 minutes followed by six washes with washing buffer at room temperature Slides were rinsed triplefold during five minutes with PBS, followed by distilled water.

The gold particles were visualized by silver enhancement during 15 minutes.

The results showed clear and sharp staining with excellent contrast.

Section 5

5.1 Detection of Specific Antibodies

Micro-arrays were printed as described previously using specific antigens such as CEA (carcino-embronal antigen) and EMA (epithelial membrane antigen). The antigens were diluted in printing buffer consisting of PBS (pH 7.4) resulting in various concentrations and were spotted in sixfold including adequate positive and negative controls using a Microcast micro-arrayer.

This results in a micro-array with 7 seven rows, each row consisting of six identical spots, representing various concentrations of the above described antibodies or antigens. The negative controls consisted of printing buffer without antigen and a second negative control consisted of a non-related antigen and were printed as two rows consisting of six spots where one row consisted out of printing buffer without antibody or antigen and another row consisted of non-related antigen.

The positive control consisted of an equimolar mixture of antibodies directed against the above described antigens printed in one row consisting of six identical spots.

After printing the micro-arrays were air dried at room temperature for 15 minutes and stored dust-free at 4° C. until use.

Slides were washed twice with PBS (pH 7.4) supplemented with 3% BSA followed by an incubation during 30 minutes at room temperature followed by incubation with anti-CEA (carcino-embryonal antigen) antibody. Slides were washed twice with PBS (pH 7.4) supplemented with BSA.

Slides were incubated with the same PBS/BSA buffer solution during 30 minutes at room temperature.

Slides were washed twice with special washing buffer (PBS pH 7.4 supplemented with BSA) during 5 minutes and incubated with the same washing buffer.

Slides were incubated with monoclonal or polyclonal antibody labelled with gold particles ranging from 0.6 nm to 40 nm during 60 minutes followed by six washes with washing-buffer at room temperature.

Slides were incubated with dextran polymer coated with numerous anti-mouse antibodies and anti-rabbit antibodies for 30 minutes followed by six washes with washing buffer.

Slides were incubated with monoclonal or polyclonal antibody labelled with gold particles ranging from 0.6 nm to 40 nm during 60 minutes followed by six washes with washing buffer at room temperature Slides were rinsed triplefold during five minutes with PBS, followed by distilled water.

The gold particles were visualized by silver enhancement during 15 minutes. The results showed clear and sharp staining with excellent contrast.

5.2 Detection of Specific Antigens

Micro-arrays were printed like described previously using specific antibodies detecting CEA.

The antibodies were diluted in printing buffer consisting of PBS (pH 7.4) resulting in various concentrations and were spotted in sixfold including adequate positive and negative controls using a Microcast micro-arrayer.

This results in a micro-array with 7 seven rows, each row consisting of six identical spots, representing various concentrations of the above described antibodies. The negative controls consisted of printing buffer without antibody or antigen and a second negative control consisted of a non-related antigen d were printed as two rows consisting of six spots where one row consisted out of printing buffer without antibody or antigen and another row consisted of non-related antibody or antigen.

The positive control consisted of an equimolar mixture of the above described antigen printed in one row consisting of six identical spots.

After printing the micro-arrays were air dried at room temperature for 15 minutes and stored dust free at 4° C. until use.

Slides were washed twice with PBS (pH 7.4) and incubated with CEA antigen. Slides were washed twice with PBS (pH 7.4) supplemented with BSA.

Slides were incubated with the same PBS/BSA buffer solution during 30 minutes at room temperature.

Slides were washed twice with special washing buffer (PBS pH 7.4 supplemented with BSA) during 5 minutes and incubated with the same washing buffer.

Slides were incubated with monoclonal or polyclonal antibody labelled with gold particles ranging from 0.6 nm to 40 nm during 60 minutes followed by six washes with washing buffer at room temperature.

Slides were incubated with dextran polymer coated with numerous anti-mouse antibodies and anti-rabbit antibodies for 30 minutes followed by six washes with washing buffer.

Slides were incubated with monoclonal or polyclonal antibody labelled with gold particles ranging from 0.6 nm to 40 nm during 60 minutes followed by six washes with washing buffer at room temperature Slides were rinsed triplefold during five minutes with PBS, followed by distilled water.

The gold particles were visualized by silver enhancement for 15 minutes.

The results showed clear and sharp staining with excellent contrast.

What is claimed is:

1. A method for quantitatively and/or qualitatively detecting one or more components in one or more samples, said component capable of binding to a probe, comprising the steps in the following order:
   a) applying onto a solid support
      i) one or more samples comprising components to be detected or
      ii) one or more probes,
   b) incubating the solid support of step a) with:
      i) one or more tagged probes, in the case where the solid support has one or more samples comprising components to be detected applied thereon, or
      ii) sample comprising tag-labeled components to be detected, in the case where the solid support has one or more probes applied thereon, said incubating followed by a wash step,
   c) incubating the solid support with a monoclonal or polyclonal antibody directed against the tag of step b), said antibody raised in species A and said antibody is labeled with metal particles of average diameter between 0.6 nm and 40 nm, followed by a wash step,
   d) incubating the solid support with an antibody conjugate, said conjugate comprising:
      one or more antibodies, anti-A, directed against immunoglobulins of species A, and
      one or more antibodies, anti-B, directed against immunoglobulins of species B, said incubating followed by a wash step,
   e) incubating the solid support with a polypeptide capable of recognition by anti-B antibodies, said polypeptide labeled with one or more substances which directly or indirectly cause a quantitative color change compared with the solid support,
   f) incubating the solid support with a metal enhancement reagent, and
   g) reading the solid support to quantitatively and/or qualitatively detect said components.

2. The method according to claim 1 wherein step a) comprises applying one or more probes onto the solid support, and step b) comprises incubating the solid support with tag-labeled components.

3. The method according to claim 1 wherein step b) comprises incubating the solid support with the tag-labeled components to be detected and wherein said antibody in step c) comprises a metal-particle-labeled anti-component monoclonal or polyclonal antibody, said antibody raised in species A.

4. The method according to claim 1 further comprising the steps, after step e), of:
   e-1) repeating steps d) to e), and
   e-2) optionally repeating step e-1).

5. The method according to claim 2 wherein the solid support is supplied with the probe pre-applied.

6. The method according to claim 1 wherein the reading of step g) comprises the use of a color chart.

7. The method according to claim 1 wherein the reading of step g) comprises the use of a device suitable for detecting changes in conductance and/or current across the solid support at positions at which said samples are applied.

8. The method according to claim 1 wherein said tag is biotin.

9. The method according to claim 1 wherein said polypeptide capable of recognition by anti-B antibodies is labeled with gold particles and/or alkaline phosphatase.

10. The method according to claim 1, further comprising storing the solid support of step a) at a temperature between 0 and 10 degrees Celsius.

11. The method according to claim 1, wherein the antibody conjugate further comprises one or more substances which directly or indirectly cause a quantitative color change compared with the solid support.

12. The method according to claim 1, further comprising incubating the solid support with a color change reagent that is a suitable substrate of an enzyme attached to the antibody conjugate after step f).

13. The method according to claim 1, wherein the metal particle is gold.

* * * * *

UNITED STATES PATENT AND TRADEMARK OFFICE
CERTIFICATE OF CORRECTION

PATENT NO. : 7,510,881 B2
APPLICATION NO. : 10/569713
DATED : March 31, 2009
INVENTOR(S) : Ramael et al.

It is certified that error appears in the above-identified patent and that said Letters Patent is hereby corrected as shown below:

Column 6, Line 61, "digoxygenin, streptavidin," should be changed to --digoxigenin, streptavidin,--

Column 7, Line 61, "Alexins, Tamra," should be changed to --Alexis, Tamra,--

Column 8, Line 38, "degrees Celcius." should be changed to --degrees Celsius.--

Column 13, Line 11, "further 30 enhances" should be changed to --further enhances--

Column 15, Line 61, "niphedipine oxidase)," should be changed to --nifedipine oxidase),--

Column 17, Line 24, "homolog (avain)" should be changed to --homolog (avian)--

Column 19, Line 70, "beta receptar II" should be changed to --beta receptor II--

Column 19, Line 73, "cytochnome P450," should be changed to --cytochrome P450,--

Column 25, Line 67, "(callagenase 3)" should be changed to --(collagenase 3)--

Column 30, Line 54, "or chemilluminescent" should be changed to --chemiluminescent--

Column 33, Line 11, "5' GGATTATTGTTAAATATTGATAAGGAT 3'" should be changed to --5' GGATTATTGTTAAATATTGATAAGGAT 3' (SEQ ID NO: 1)--

Column 33, Line 12, "5' ATCCTTATCAATATT 3'" should be changed to --5' ATCCTTATCAATATT 3' (SEQ ID NO: 2)--

Column 33, Line 15, "5' TAACAATAATCC 3'" should be changed to --5' TAACAATAATCC 3' (SEQ ID NO: 3)--

Column 33, Line 25, "Mofified DNA" should be changed to --Modified DNA--

UNITED STATES PATENT AND TRADEMARK OFFICE
CERTIFICATE OF CORRECTION

PATENT NO. : 7,510,881 B2
APPLICATION NO. : 10/569713
DATED : March 31, 2009
INVENTOR(S) : Ramael et al.

It is certified that error appears in the above-identified patent and that said Letters Patent is hereby corrected as shown below:

Column 35, Line 51, "phosphatase enzym" should be changed to --phosphatase enzyme--

Column 42, Line 55, "signal strenghtening." should be changed to --signal strengthening.--

Column 43, Line 5, "the used enzym" should be changed to --the used enzyme--

Column 43, Line 57, "acieved with spotted" should be changed to --achieved with spotted--

Column 44, Line 49, "enzym method." should be changed to --enzyme method.--

Column 45, Line 8, "enzym method." should be changed to --enzyme method.--

Column 47, Line 18, "during 15 minutes" should be changed to --during 15 minutes.--

Column 48, Line 20, "in an descending" should be changed to --in a descending--

Signed and Sealed this

Twenty-fifth Day of August, 2009

David J. Kappos
*Director of the United States Patent and Trademark Office*

SEQUENCE LISTING

```
<160> NUMBER OF SEQ ID NOS: 3

<210> SEQ ID NO 1
<211> LENGTH: 27
<212> TYPE: DNA
<213> ORGANISM: Artificial Sequence
<220> FEATURE:
<223> OTHER INFORMATION: chemically synthesized

<400> SEQUENCE: 1
ggattattgt taaatattga taaggat                                    27

<210> SEQ ID NO 2
<211> LENGTH: 15
<212> TYPE: DNA
<213> ORGANISM: Artificial Sequence
<220> FEATURE:
<223> OTHER INFORMATION: chemically synthesized

<400> SEQUENCE: 2
atccttatca atatt                                                15
```

```
<210> SEQ ID NO 3
<211> LENGTH: 12
<212> TYPE: DNA
<213> ORGANISM: Artificial Sequence
<220> FEATURE:
<223> OTHER INFORMATION: chemically synthesized

<400> SEQUENCE: 3
taacaataat cc                                                            12
```